(12) United States Patent
Satomi et al.

(10) Patent No.: US 7,462,757 B2
(45) Date of Patent: Dec. 9, 2008

(54) ANIMAL WITH GENE HYPOEXPRESSION

(75) Inventors: Tomoko Satomi, Osaka (JP); Ryuichi Tozawa, Osaka (JP); Mitsugu Nakata, Osaka (JP); Yoshitaka Yasuhara, Osaka (JP); Yoshio Taniyama, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 536 days.

(21) Appl. No.: 10/478,466

(22) PCT Filed: May 21, 2002

(86) PCT No.: PCT/JP02/04876

§ 371 (c)(1),
(2), (4) Date: Nov. 21, 2003

(87) PCT Pub. No.: WO02/102998

PCT Pub. Date: Dec. 27, 2002

(65) Prior Publication Data

US 2004/0143862 A1 Jul. 22, 2004

(30) Foreign Application Priority Data

May 22, 2001 (JP) ............................. 2001/152520
Oct. 9, 2001 (JP) ............................. 2001/311971

(51) Int. Cl.
*A01K 67/00* (2006.01)
*A01K 67/027* (2006.01)
*G01N 33/00* (2006.01)

(52) U.S. Cl. .................... 800/18; 800/3; 800/8; 800/9; 800/14

(58) Field of Classification Search .................. 800/3, 800/8, 9, 14
See application file for complete search history.

(56) References Cited

U.S. PATENT DOCUMENTS 6,498,019 B1 12/2002 Taniyama
7,157,259 B2 1/2007 Taniyama

FOREIGN PATENT DOCUMENTS

JP    H11-269199    10/1999
WO    WO-00/078789  12/2000

OTHER PUBLICATIONS

Taniyama et al, Biochem Biophys Res Commun.330(1):104-110, 2005.*
Wood. Comp. Med. 50(1): 12-15, 2000.*
Sigmund, Arterioscler. Throm. Vasc. Biol.20:1425-1429, 2000.*
Wall RJ Theriogenology 45:57-68, 1996.*
Pursel VG et al J. Reprod Fert. Sup 40: 235-245 1990.*
Kappel et al. Current Opinion in Biotechnology 3:548-553 1992.*
Viville, in Transgenic Animals, Houdebine (eds).*
Ng et al. J Bio. Chem. 272(25):14777-15781, 1997.*
Wall, Cloning & Stem Cells 3(4): 209-220, 2001.*
Piedrahita J A et al: "Generation of Mice Carrying a Mutant Apolipoprotein E Gene Inactivated by Gene Targeting in Embryonic Stem Cells": Proceedings of the National Academy of Sciences of USA, National Academy of Science, Washington, US, vol. 89, No. 10, May 1992, pp. 4471-4475, XP002290504, ISSN: 0027-8424.
Zhang S H et al: "Spontaneous Hypercholesterolemia and Arterial Lesions in Mice Lacking Apolipoprotein E": Science, American Association for the Advancement of Science, US, vol. 258, No. 5081, Oct. 16, 1992, pp. 468-471, XP001183032, ISSN: 0036-8075.
Hiraoka M et al: "Cloning and Characterization of a Lysosomal Phospolipase A2, 1-O-Acylceramide Synthase": Journal of Biological Chemistry, American Society of Biological Chemists, Baltimore, MD, US, vol. 277, No. 12, Mar. 22, 2002, pp. 10090-10099, XP002967695, ISSN: 0021-9258.
Y. Taniyama et al., "Cloning and Expression of a Novel Lysophospholipase Which Structurally Resembles Lecithin Cholesterol Acyltransferase", Biochem. Biophys. Res. Commun., vol. 257, No. 1, pp. 50-56 (1999).

* cited by examiner

*Primary Examiner*—Sumesh Kaushal
(74) *Attorney, Agent, or Firm*—David G. Conlin; Elizabeth N. Spar; Edwards Angell Palmer & Dodge LLP

(57) ABSTRACT

The present invention relates to non-human animal embryonic stem cells in which a lecithin:cholesterol acyltransferase-like lysophospholipase endogenous gene is inactivated; non-human animals deficient in expression of LLPL gene; methods of screening for prophylactics and/or therapeutic drug using the cells or the animals; and prophylactics and/or therapeutic drug obtainable by the screening.

The non-human animal ES cells of the invention in which their LLPL gene is inactivated are very useful in creating non-human animals deficient in expression of LLPL gene. The LLPL expression deficient non-human animals of the invention can be disease models for such diseases caused by insufficiency of the biological activities of LLPL since the animals lack various biological activities inducible by LLPL. Therefore, the animals of the invention are useful in screening for prophylactics and/or therapeutic drug for various diseases resulting from LLPL deficiency, as well as in elucidating the causes of LLPL-related diseases and examining therapeutic methods for such diseases. The screening methods of the invention are capable of efficiently screening for prophylactics and/or therapeutic drug for various diseases resulting from LLPL deficiency.

4 Claims, 13 Drawing Sheets

Fig. 7
Wild-type  Homo-deficient
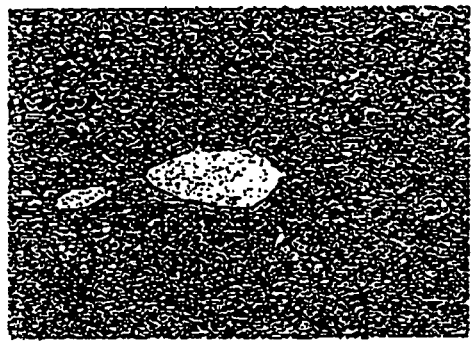
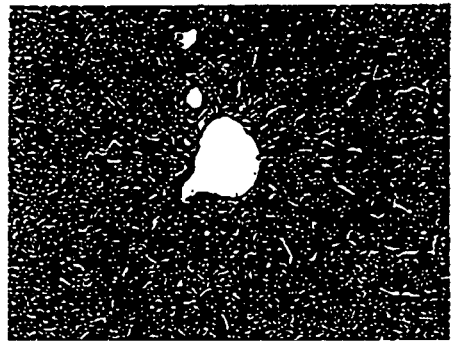
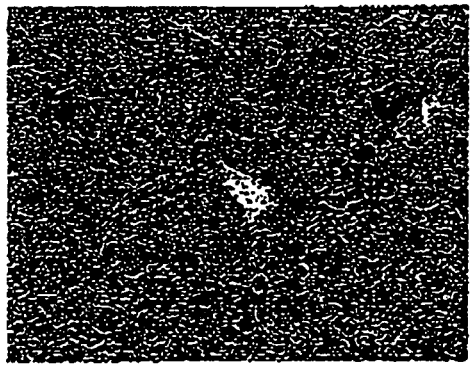
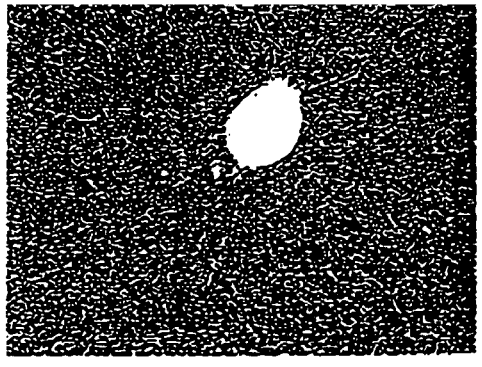

Mean ± SD (n=5-8), *: p<0.05, **: p<0.01 vs WT (Student's T-test)

```
SEQUENCE LISTING

<160> NUMBER OF SEQ ID NOS: 7

<210> SEQ ID NO 1
<211> LENGTH: 412
<212> TYPE: PRT
<213> ORGANISM: Mouse

<400> SEQUENCE: 1

Met Asp Arg His Leu Cys Thr Cys Arg Glu Thr Gln Leu Arg Ser Gly
 1               5                   10                  15

Leu Leu Leu Pro Leu Phe Leu Leu Met Met Leu Ala Asp Leu Thr Leu
            20                  25                  30

Pro Ala Gln Arg His Pro Pro Val Val Leu Val Pro Gly Asp Leu Gly
        35                  40                  45

Asn Gln Leu Glu Ala Lys Leu Asp Lys Pro Lys Val Val His Tyr Leu
    50                  55                  60
```

```
Cys Ser Lys Lys Thr Asp Ser Tyr Phe Thr Leu Trp Leu Asn Leu Glu
 65                  70                  75                  80

Leu Leu Leu Pro Val Ile Ile Asp Cys Trp Ile Asp Asn Ile Arg Leu
                 85                  90                  95

Val Tyr Asn Arg Thr Ser Arg Ala Thr Gln Phe Pro Asp Gly Val Asp
            100                 105                 110

Val Arg Val Pro Gly Phe Gly Glu Thr Phe Ser Met Glu Phe Leu Asp
        115                 120                 125

Pro Ser Lys Arg Asn Val Gly Ser Tyr Phe Tyr Thr Met Val Glu Ser
    130                 135                 140

Leu Val Gly Trp Gly Tyr Thr Arg Gly Glu Asp Val Arg Gly Ala Pro
145                 150                 155                 160

Tyr Asp Trp Arg Arg Ala Pro Asn Glu Asn Gly Pro Tyr Phe Leu Ala
                165                 170                 175

Leu Arg Glu Met Ile Glu Glu Met Tyr Gln Met Tyr Gly Gly Pro Val
            180                 185                 190

Val Leu Val Ala His Ser Met Gly Asn Val Tyr Met Leu Tyr Phe Leu
        195                 200                 205

Gln Arg Gln Pro Gln Val Trp Lys Asp Lys Tyr Ile His Ala Phe Val
    210                 215                 220

Ser Leu Gly Ala Pro Trp Gly Gly Val Ala Lys Thr Leu Arg Val Leu
225                 230                 235                 240

Ala Ser Gly Asp Asn Asn Arg Ile Pro Val Ile Gly Pro Leu Lys Ile
                245                 250                 255

Arg Glu Gln Gln Arg Ser Ala Val Ser Thr Ser Trp Leu Leu Pro Tyr
            260                 265                 270

Asn His Thr Trp Ser His Glu Lys Val Phe Val Tyr Thr Pro Thr Thr
        275                 280                 285

Asn Tyr Thr Leu Arg Asp Tyr His Arg Phe Phe Arg Asp Ile Gly Phe
    290                 295                 300

Glu Asp Gly Trp Phe Met Arg Gln Asp Thr Glu Gly Leu Val Glu Ala
305                 310                 315                 320

Met Thr Pro Pro Gly Val Glu Leu His Cys Leu Tyr Gly Thr Gly Val
                325                 330                 335

Pro Thr Pro Asn Ser Phe Tyr Tyr Glu Ser Phe Pro Asp Arg Asp Pro
            340                 345                 350

Lys Ile Cys Phe Gly Asp Gly Asp Gly Thr Val Asn Leu Glu Ser Val
        355                 360                 365

Leu Gln Cys Gln Ala Trp Gln Ser Arg Gln Glu His Arg Val Ser Leu
    370                 375                 380

Gln Glu Leu Pro Gly Ser Glu His Ile Glu Met Leu Ala Asn Ala Thr
385                 390                 395                 400

Thr Leu Ala Tyr Leu Lys Arg Val Leu Leu Glu Pro
                405                 410

<210> SEQ ID NO 2
<211> LENGTH: 1236
<212> TYPE: DNA
<213> ORGANISM: Mouse

<400> SEQUENCE: 2
atggatcgcc atctctgcac ctgtcgcgag acccagctcc ggagtggcct cctgttacct    60
ctgtttctac taatgatgct ggcagacctg acgctcccgg cccaacgtca ccccccggtg   120
gtgctggtgc ctggtgattt gggtaaccag ttggaagcaa agctggataa gccaaaggtt   180
```

```
gtacactacc tttgctccaa gaagacggac agctacttca cactctggct gaatctggaa    240
ctgcttctgc ctgttatcat tgactgctgg attgacaata tcaggctggt ttacaacaga    300
acatctcggg ccacccagtt tcccgatggt gtggacgtgc gtgtccctgg ctttggggaa    360
acattttcta tggaattcct agaccccagc aagaggaatg tgggttccta tttctacact    420
atggtggaga gccttgtggg ctggggctac acacggggtg aagacgttcg aggtgctccc    480
tatgattggc ggcgagcccc aaatgaaaac gggccctact tcttggccct gcgagagatg    540
atcgaggaga tgtaccagat gtatgggggc cccgtggtgc tggtcgccca gcatgggc      600 aacgtgtaca tgctctactt tctgcagcgg cagccacaag tctggaagga caaatatatc    660
catgccttcg tctcactggg ggcgccctgg ggggcgtgg ccaagacgct gcgtgtcctg     720
gcctcaggag acaacaatcg cattcccgtc attgggccac tgaagatccg ggaacagcag    780
cgatctgccg tctctaccag ctggctactg ccatacaacc acacttggtc acatgaaaag    840
gtatttgtat acacacccac gactaactac acgctccggg actatcaccg gttcttccgg    900
gacatcggtt tcgaagatgg ctggttcatg cggcaggaca cagaagggct ggttgaagcc    960
atgacgccac ccggggtgga gctgcactgc ttgtatggca ctggtgttcc cacgccaaac   1020
tctttctact acgagagctt tcctgatcgg accccaaaa tctgcttcgg cgatggtgac    1080
ggcacggtga acctggagag cgtcctgcag tgccaagcct ggcagagccg ccaagagcac   1140
agagtatcat tgcaggagct gccgggaagc gagcacattg agatgctagc caatgccacc   1200
accttggctt atctgaaacg tgtgcttctg gaacct                             1236

<210> SEQ ID NO 3
<211> LENGTH: 21
<212> TYPE: DNA
<213> ORGANISM: Artificial Sequence
<220> FEATURE:
<223> OTHER INFORMATION: primer P94-1

<400> SEQUENCE: 3
ggtaaccagt tggaagcaaa g                                                21

<210> SEQ ID NO 4
<211> LENGTH: 16
<212> TYPE: DNA
<213> ORGANISM: Artificial Sequence
<220> FEATURE:
<223> OTHER INFORMATION: primer P101-4

<400> SEQUENCE: 4
ccccgggtgg cgtcat                                                      16

<210> SEQ ID NO 5
<211> LENGTH: 26
<212> TYPE: DNA
<213> ORGANISM: Artificial Sequence
<220> FEATURE:
<223> OTHER INFORMATION: primer SI-75

<400> SEQUENCE: 5
gattgggaag acaatagcag gcatgc                                           26

<210> SEQ ID NO 6
<211> LENGTH: 26
<212> TYPE: DNA
<213> ORGANISM: Artificial Sequence
<220> FEATURE:
```

```
<223> OTHER INFORMATION: primer P3-t

<400> SEQUENCE: 6
tggtgcaagt attatcaccg cccatt                                        26

<210> SEQ ID NO 7
<211> LENGTH: 26
<212> TYPE: DNA
<213> ORGANISM: Artificial Sequence
<220> FEATURE:
<223> OTHER INFORMATION: primer P4-s

<400> SEQUENCE: 7
cgctcatctg atcatcgtaa tgatcg                                        26
```

ANIMAL WITH GENE HYPOEXPRESSION

This application is a U.S. national phase application, pursuant to 35 U.S.C. §371, of PCT international application Ser. No. PCT/JP02/04876 filed May 21, 2002, designating the United States, and published in Japanese as international publication WO 02/102998 on Dec. 27, 2002, which claims priority to Japanese patent application Ser. No. 311971/2001 filed on Oct. 9, 2001, and to Japanese patent application Ser. No. 152520/2001 filed on May 22, 2001. The entire contents of the aforementioned patent applications are incorporated herein by this reference.

TECHNICAL FIELD

The present invention relates to non-human mammal embryonic stem cells in which the endogenous gene encoding lecithin: cholesterol acyltransferase-like lysophospholipase (LCAT-like lysophospholipase; hereinafter, sometimes abbreviated to "LLPL") is inactivated; non-human mammals deficient in expression of LLPL gene; methods of screening for prophylactic and/or therapeutic drug using the ES cells or the non-human mammals; and prophylactic and/or therapeutic drug obtainable by the methods.

BACKGROUND ART

As the technology of genetic engineering has advanced and the knowledge of molecular biology, the basis for that technology, has been accumulated rapidly, it has become possible to manipulate genes artificially and yet to introduce them into animals [Gordon, J. W. et al., Proc. Natl. Acad. Sci. U.S.A. 77:7380-7384 (1980)]. For example, methods for artificially adding to organisms genetic characters which are foreign to them or methods for inhibiting the expression of endogenous genetic characters in organisms have been developed. By utilizing such methods, animals into which various genetic characters are introduced have been created and reported as transgenic animals or knockout animals.

These transgenic animals are important from the view point that they make it possible to study the functions of various genes isolated and cloned by genetic engineering technologies at the individual level. So far, gene functions have been studied using ex vivo cultured cells, such as cell lines or primary culture cells, and findings obtainable from such study have been rather limited. In particular, experiments and researches have been vigorously made in which such transgenic animals are used for analyzing in vivo physiological functions of cloned genes or used as model animals for genetic diseases.

Embryonic stem cells (hereinafter, referred to as "ES cells") are a cell strain which is established from the internal cell mass present inside of a blastocyst (early embryo after fertilization) and can be grown/cultured while retaining the undifferentiated state. These cells have pluripotency (totipotence) i.e. the ability to differentiate into any cell in the body. When injected into a normal early embryo, they are capable of participating in the formation of the embryo to generate a chimeric animal [Evans, M. J. and Kaufman M. H., Nature 292:154 (1981)].

Creation of various gene-mutated animals has been attempted utilizing this nature of ES cells. The history began with the establishment of ES cells by Evans and Kaufman in 1981, and earnest researches started with the creation of ES chimeric mice by Bradley et al. [Nature 309:255 (1984)]. Further, researches in this field have developed rapidly, e.g. homologous recombination of ES cells by Thomas and Capecchi [Cell 51:503 (1987)]; success in germ line transmission of ES cell characters by three research groups including Koller et al.; and creation of gene-deficient mice.

ES cell lines established so far include EK cells of Evans and Kaufman (supra); ES-D3 cells of Doetschman [J. Embryol. Exp. Molph. 87:27 (1981)]; CCE cells of Robertson [Nature 323:445 (1986)]; and BL/6III cells of Ladermann and Burki [Exp. Cell Res. 197:254]. Most of them are established from 129 strain mice.

As gene expression-deficient animals created with these ES cells, the following animals have been reported: (I) HPRT gene deficient mice created with spontaneous mutant ES cells by Hooper et al. [Nature 326:292 (1987)] and Knehn et al. [Nature 326:295 (1987)]; (2) p53 deficient mice which lack p53, one of tumor suppressor genes, by Donehower et al. [Nature 356:215 (1992)]; (3) β 2 microglobulin gene mutant mice by Zijlstra et al. [Nature 344:742 (1990)]; (4) RAG-2 (V(D)J recombination activation gene) mutant mice by Sinkai et al. [Cell 68:855 (1992)] which is one of disease model mice; (5) MHC class II mutant mice by Glimcher et al. [Science 253:1417 (1991)] and Cosgrove et al. [Cell 66:1051 (1991)]; (6) as one of development/growth related disease model mice, int-1 gene deficient mice by MacMahon et al. [Cell 62:1073 (1990)]; and (7) src deficient mice exhibiting osteopetrosis-like symptoms by Soriano et al. [Cell 64:693 (1991)].

On the other hand, a number of molecules, such as apoproteins [Srivastava R. & A. Srivastava, N., Mol. Cell Biochem. 209:131-144 (2999)], enzymes, receptors [Hiltumen, T. P. & Yla-Herttuala, S., Atherosclerosis 137:S81-88 (1988)] and lipid transfer proteins [Yamashita, S. et al., Atherosclerosis 152:271-285 (2000); Oram, J. F. & Vaughan, A. M., Curr. Opin. Lipidol., 11:253-260 (2000)], are involved in the metabolism of lipoproteins. Differences among individuals resulted from different genetic types of these proteins or brought by different diet are closely related to arteriosclerosis. High-density lipoprotein (HDL)-cholesterol, which is one of such proteins, is recognized by a number of epidemiological researches as an independent negative risk factor for coronary artery diseases [Barter, P. J. & Rye, K A., Atherosclerosis 121:1-12 (1996)]. HDL plays an important role in the so-called cholesterol reverse-transfer system which extracts excessive cholesterol from peripheral tissues and transfers the cholesterol to the liver [Tall, A. et al., Arterioscler. Thromb. Vasc. Biol., 20:1185-1188 (2000); Santamarina-Fojo, S. et al., Curr. Opin. Lipidol., 11:267-75 (2000)]. Lecithin:cholesterol acyltransferase (LCAT), which is the rate-determining enzyme in the system, is produced mainly in the liver [Warden, C. et al., J. Biol. Chem. 264:21573-21581 (1989)] and is present in HDL particles in blood [Kuivenhoven, J. et al., J. Lipid Res. 38:191-205 (1997)]. The free cholesterol extracted from peripheral cells by pre β HDL is esterified by LCAT, and thus the flow of cholesterol into cells is inhibited. As a result, LCAT exhibits cholesterol extraction-promoting effect, and it is believed that LCAT functions in an anti-arteriosclerotic manner [Czarnecka, H. & Yokoyama, S., Biochemistry 34:4385-92 (1995)]. Recently, an enzyme LLPL that has 47% homology to human LCAT at the amino acid level has been found by subtraction PCR using a cDNA library of human macrophage-like cells, and the full-length amino acid sequence thereof has been determined by cDNA analysis [Taniyama et al., Biochem. Biophys. Res. Commun. 257:50-56 (1999)].

Large quantities of macrophages transformed into foam cells are accumulated in human arteriosclerosis lesions. Besides, it is known that LLPL is secreted in human macrophage-like cells and that ApoE (apolipoprotein E) gene is one of the genes associated with arteriosclerosis. The results of in situ hybridization using arteriosclerosis lesions of an arteriosclerosis model mouse (ApoE deficient mouse) revealed that mouse LLPL gene is expressed in those lesions. Thus, it is considered that LLPL gene is closely related to the progress of arteriosclerosis.

Although human LLPL does not have the LCAT activity to esterify free cholesterol, it exhibits the lysophospholipase activity to degrade free cholesterol into free fatty acids and glycerophosphorylcholine in vitro using lysophosphatidylcholine as a substrate [Taniyama et al., Biochem. Biophys. Res. Commun. 257:50-56 (1999)]. Further, it has been also confirmed that human LLPL is present in human serum. The presence of unidentified substrate in serum is suggested.

It is known that LLPL is secreted in macrophage-like cells in human and in peritoneal macrophages in mouse; and that human LLPL and mouse LLPL are 88% homologous in the amino acid sequence and their lipase motifs are the same AHSMG sequence (Japanese Unexamined Patent Publication No. 11-269199). In both human and mouse, LLPL gene is expressed specifically in peripheral tissues. Thus, human LLPL and mouse LLPL have a number of similarities. Further, since expression of LLPL is confirmed in arteriosclerosis lesions of ApoE-deficient mice, it is believed that LLPL has effects upon arteriosclerosis lesions and plasma lipid profile.

However, these effects have not been elucidated sufficiently and there are many issues of which should be clarified with regard to in vivo functions of LLPL and the mechanism thereof. Animal models deficient in expression of LLPL gene which produce no or little LLPL are indispensable for elucidating the in vivo effects of LLPL and desired eagerly. However, no such animal models have been created to date.

Therefore, if non-human animal ES cells where their LLPL gene is inactivated have been successfully created, it is possible to create non-human animals deficient in expression of LLPL gene. Since the resultant non-human animals deficient in expression of LLPL gene lack various biological activities inducible by LLPL, they can be models for such diseases resulting from inactivation of the biological activities of LLPL. With such animal models, it becomes possible to elucidate the causes of such diseases and to examine therapeutic methods for such diseases.

DISCLOSURE OF THE INVENTION

As a result of extensive and intensive researches toward solution of the above-mentioned problems, the present inventors have succeeded in creating a non-human animal deficient in expression of LLPL gene. Then, further researches have been made and, as a result, the present invention has been achieved.

The present invention provides:
(1) A mammalian embryonic stem cell wherein lecithin:cholesterol acyltransferase-like lysophospholipase gene thereof is inactivated;
(2) The embryonic stem cell of (1) above, wherein the cell is drug resistant;
(3) The embryonic stem cell of (2) above, wherein the drug is a neomycin;
(4) The embryonic stem cell of (1) above, wherein lecithin:cholesterol acyltransferase-like lysophospholipase gene thereof is inactivated by insertion of a reporter gene;
(5) The embryonic stem cell of (4) above, wherein the reporter gene is a lacZ gene;
(6) The embryonic stem cell of (1) above, wherein the mammal is a rodent;
(7) The embryonic stem cell of (6) above, wherein the rodent is mouse;
(8) A non-human mammal deficient in expression of lecithin:cholesterol acyltransferase-like lysophospholipase gene thereof or a tissue thereof, or cells derived from the mammal or tissue;
(9) The animal, a tissue thereof, or cells derived from the animal or tissue of (8) above, wherein the non-human mammal is a rodent;
(10) A method of screening for a prophylactic and/or therapeutic drug for a disease resulting from deficiency of lecithin:cholesterol acyltransferase-like lysophospholipase gene, comprising using the animal, a tissue thereof or cells derived from the animal or tissue of (8) above;
(11) A method of screening for a prophylactic and/or therapeutic drug for a disease resulting from deficiency of lecithin:cholesterol acyltransferase-like lysophospholipase gene, comprising administering a test compound to the animal, a tissue thereof or cells derived from the animal or tissue of (8) above;
(12) The method of screening of (10) or (11) above, therein the disease is arteriosclerosis;
(13) A prophylactic and/or therapeutic drug for a disease resulting from deficiency of lecithin:cholesterol acyltransferase-like lysophospholipase gene, which is obtainable by the method of screening of (10) or (11) above;
(14) The prophylactic and/or therapeutic drug of (13) above, wherein the disease is arteriosclerosis;
(15) A disease model animal, or a tissue thereof, generated by mating the animal of (8) above with other disease model animal, or cells derived from the generated disease model animal or a tissue thereof;
(16) A disease model animal, or a tissue thereof, generated by subjecting the animal of (8) above to drug induction or by loading stress on said animal, or cells derived from the generated disease model animal or a tissue thereof;
(17) The disease model animal, a tissue thereof or cells derived from the animal or tissue of (15) above, wherein the other disease model animal is a non-human mammal deficient in expression of its apolipoprotein gene;
(18) The disease model animal, a tissue thereof or cells derived from the animal or tissue of (17) above, wherein the non-human mammal is a non-human mammal which is double-deficient in lecithin:cholesterol acyltransferase-like lysophospholipase gene and apolipoprotein gene;
(19) The disease model animal, a tissue thereof or cells derived from the animal or tissue of (17) above, wherein the apolipoprotein is apolipoprotein E;
(20) A disease model animal, or a tissue thereof, generated by subjecting the animal of (15) above to drug induction or by loading stress on said animal, or cells derived from the generated disease model animal or a tissue thereof;
(21) A method of screening for a prophylactic and/or therapeutic drug for a disease resulting from deficiency of lecithin:cholesterol acyltransferase-like lysophospholipase gene, comprising using the animal, a tissue thereof or cells derived from the animal or tissue of any one of (15) to (17) and (20) above;
(22) A method of screening for a prophylactic and/or therapeutic drug for a disease resulting from deficiency of lecithin:cholesterol acyltransferase-like lysophospholipase gene, comprising administering a test compound to the animal, a tissue thereof or cells derived from the animal or tissue of any one of (15) to (17) and (20) above;
(23) A prophylactic and/or therapeutic drug for a disease resulting from deficiency of lecithin:cholesterol acyltransferase-like lysophospholipase gene, which is obtainable by the method of screening of (22) or (23);

(24) A method of screening for a prophylactic and/or therapeutic drug for a disease resulting from deficiency of lecithin:cholesterol acyltransferase-like lysophospholipase gene, comprising using the animal, a tissue thereof or cells derived from the animal or tissue of (17) above;

(25) A method of screening for a prophylactic and/or therapeutic drug for a disease resulting from deficiency of lecithin:cholesterol acyltransferase-like lysophospholipase gene, comprising administering a test compound to the animal, a tissue thereof or cells derived from the animal or tissue of (17) above; and

(26) A prophylactic and/or therapeutic drug for a disease resulting from deficiency of lecithin:cholesterol acyltransferase-like lysophospholipase gene, which is obtainable by the method of screening of (24) or (25) above.

BRIEF DESCRIPTION OF THE DRAWINGS

FIG. 7 shows histopathological examination of the liver from wild-type mouse group and homo-deficient mouse group obtained in Example 4 both fed with a high cholesterol high lipid diet for 16 weeks. Upper panel shows specimen stained with hematoxylin-eosin (H&E) (×100). The lower panel shows specimen stained with lipid (oil red 0) (×100). In the wild-type group, the following are observed: vacuolation of the hepatocyte cytoplasm throughout the lobe, disturbance of trabecular structure, varied sizes of nuclei due to hepatocyte regeneration, single cell necrosis in hepatocytes, mononuclear cell infiltration, and accumulation of diffuse neutral lipids. In the homo-deficient mouse group, centrilobular vacuolation of the hepatocyte cytoplasm and varied sizes of hepatocyte nuclei are observed; centrilobular accumulation of neutral lipids and accumulation of lipids are less than those in the wild-type group.

BEST MODES FOR CARRYING OUT THE INVENTION

[LLPL Gene-Inactivated Mammal ES Cells]

Figure 1:
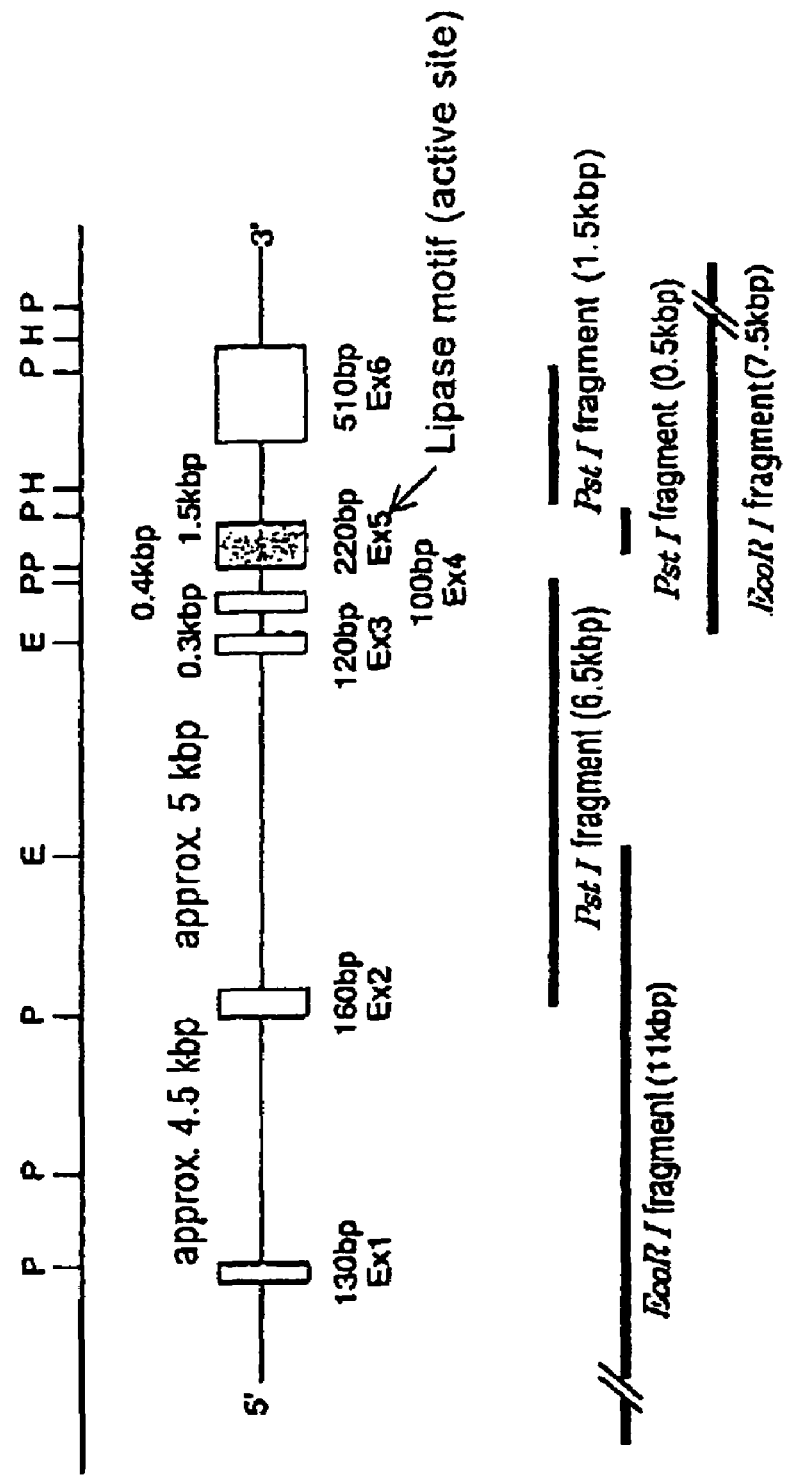
FIG. 1 shows the exon/intron structure of LLPL gene on mouse genome. In this Figure, exons are shown as boxes and introns are drawn with solid line. Five DNA fragments obtained by restriction enzyme treatment and subcloned are drawn with bold solid line.

The term "mammalian ES cell wherein its LLPL gene is inactivated" means an ES cell of a mammal in which the LLPL gene has been substantially deprived of the capacity to express LLPL protein (hereinafter, sometimes referred to as the "knockout gene of the invention") through introduction of an artificial mutation to the endogenous LLPL gene possessed by the mammal ES cell to thereby inhibit expression of the LLPL gene or through substantial deprivation of the activity of the LLPL encoded by the gene.

As mammals which may be used as materials for ES cells, human, bovine, pig, sheep, goat, rabbit, dog, cat, guinea pig, hamster, mouse, rat, etc. may be enumerated.

As non-human animals, any animal other than human having LLPL gene may be used. Preferably, non-human mammals are used. Examples of non-human mammals useful in the invention include, but not limited to, bovine, pig, sheep, goat, rabbit, dog, cat, guinea pig, hamster, mouse and rat From the viewpoint of construction of disease animal models, rodents which have relatively short ontogenesis and life cycles and can be easily propagated, particularly mouse (e.g. pure strains such as C57B/6, DBA2, etc. and hybrid strains such as B6C3F$_1$, BDF$_1$, B6D2F$_1$, BALB/c, ICR, etc.) or rat (e.g. Wistar, SD, etc.), are preferred.

Examples of methods for introducing an artificial mutation to LLPL gene are deletion of some or all of the gene sequence, or insertion of other gene, or substitution with other gene by the genetic engineering technology. The knockout LLPL gene of the invention can be created by shifting the reading frame of codons or destroying the function of the promoter or exon through the introduction of such a mutation.

For the purpose of creating a mammal (preferably, non-human mammal) ES cell wherein the LLPL gene is inactivated (hereinafter, referred to as the "LLPL gene-inactivated ES cell" or "knockout ES cell"), a DNA vector is prepared which has a DNA sequence constructed so that the exon function of LLPL gene is destroyed by insertion of a drug-resistance gene (e.g. neomycin resistance gene, hygromycin resistance gene, or zeocin resistance gene; preferably, neomycin resistance gene) or a reporter gene [e.g. lacZ (*E. coli* β-galactosidase gene), cat (chloramphenicol acetyltransferase gene), GUS (β-glucuronidase gene), luciferase gene, aequorin gene, thaumarin gene, GFP (green fluorescent protein) gene; preferably, lacZ] into its exon region, or a DNA sequence for terminating gene transcription (e.g. poly A addition signal) in an intron region between exons to thereby inhibit synthesis of a complete mRNA (hereinafter, this DNA vector is referred to as the "targeting vector"). When destruction of the exon function by insertion of a reporter gene is intended, it is preferable to insert the reporter gene so that it is expressed under the control of the LLPL promoter.

The "drug-resistance gene" mentioned above means a gene involved in resistance to antibiotics, etc. and is used as a marker for selecting whether a transferred gene is expressed in the relevant cell or not.

The "reporter gene" mentioned above refers to a group of genes which can be an indicator of gene expression. Usually, structural gene of enzymes which catalyze a luminescent reaction or a color developing reaction are used. Preferable reporter genes are (1) those which do not have genetic background; (2) those which have a highly sensitive method for quantitatively determining gene expression; (3) those which have less effect on transformed cells; and (4) those which can indicate the localization of expression site [Plant Cell Engineering, 2:721 (1990)]. The drug-resistance gene described above may be used for the same purpose. However, with the use of a reporter gene, it is possible to know not only whether the transferred gene is expressed in the cell or not. It is possible to know in which tissue and when the gene was expressed, as well as the exact amount of expression.

Subsequently, the above-described targeting vector is introduced into chromosomes of ES cells by, for example, homologous recombination. The resultant ES cells are analyzed by Southern hybridization using as a probe a DNA sequence on the LLPL gene or in the vicinity thereof; or analyzed by PCR using as primers a DNA sequence on the targeting vector and a DNA sequence in the vicinity of the LLPL gene other than the sequence used for preparing the targeting vector. Thus, the knockout ES cell of the invention can be selected.

As the targeting vector, examples of vectors useful in the invention include plasmids derived from *Escherichia coli* (e.g. pBR322, pBR325, pUC12, and pUC13); plasmids derived from *Bacillus subtilis* (e.g. pUB110, pTP5 and pC194); plasmids derived from yeast (e.g. pSH19 and pSH15); bacteriophages such as λ-phage; animal viruses such as retroviruses (e.g. Moloney leukemia virus), vaccinia virus or adenovirus vector, baculovirus, bovine papilloma virus, virus from herpes virus group, or Epstein-Barr virus.

The original ES cell used for inactivation of the endogenous LLPL gene by homologous recombination or the like may be an already established cell line such as those described hereinbefore or a new cell line established de novo by the known method of Evans and Kaufman. Taking mouse ES cells as an example, ES cells of mouse 129 strain are generally employed but the immunological background of this strain is not clear. Therefore, the cell line established by using C57BL/6 mice or $BDF_1$ mice created by crossing C57BL/6 mice with DBA/2 mice to improve the low egg output in C57BL/6 ($BDF_1=F_1$ of C57BL/6 and DBA/2) for obtaining pure-line ES cells with immunologically defined genetic background may also be used favorably. In addition to the advantages of high egg output and sturdiness of the eggs, $BDF_1$ mice have the genetic background of C57BL/6 mice. Therefore, when a disease model mouse has been created from ES cells obtained from $BDF_1$ mice, the genetic background of the resultant model mouse can be replaced with that of C57BL/6 by back-crossing with C57BL/6 mouse. Thus, $BDF_1$ mice may be used advantageously.

Moreover, in establishing ES cells, it is common practice to use blastocytes 3.5 days after fertilization. Alternatively, a large number of early embryos can be obtained efficiently by harvesting embryos at the 8-cell stage and culturing them into blastocytes.

The secondary screening can be carried out, for example, by confirming the number of chromosomes by G-banding method. The number of chromosomes in the resulting ES cell is preferably 100% of the normal number but this goal may not be reached due to the physical and other factors involved in the establishment of the ES cell. In such cases, it is preferable to knockout the gene of interest in the ES cell and re-clone it into a normal cell (in mouse, for example, those cells in which the number of chromosomes is 2n=40).

The thus obtained ES cell clone is generally very good in proliferation but it is liable to lose its ontogenic ability. Therefore, the cell clone must be subcultured with sufficient care. For example, this cell line should be cultured on suitable feeder cells such as STO fibroblasts in the presence of LIF (1-10000 U/ml) in a carbon dioxide incubator (preferably 5% $CO_2$ and 95% air, or 5% oxygen, 5% $CO_2$ and 90% air) at about 37° C. At the time of subculturing, cells should be treated with trypsin/EDTA solution (usually 0.001-0.5% trypsin/0.1-5 mM EDTA, preferably about 0.1% trypsin/1 mM EDTA) to yield single cells and the plated on freshly prepared feeder cells. While such subculturing is usually performed every 1-3 days, it is good practice to observe the cells on each occasion and, whenever morphologically abnormal cells are discovered, discard the culture.

ES cells can be allowed to differentiate into various types of cells, such as head long muscle cells, visceral muscle cells, myocardial cells, etc. by conducting monolayer culture up to a high density under suitable conditions or suspension culture until cell masses are formed (M. J. Evans & M. H. Kaufman, Nature, 292:154, 1981; G. R. Martin, Proc. Natl. Acad. Sci. USA, 78:7634, 1981; T. C. Doetschman et al., Journal of Embryology and Experimental Morphology, 87:27, 1985). The cell deficient in expression of LLPL gene that is obtainable by differentiating the ES cell of the invention is useful in cell biological examination of LLPL in vitro.

With respect to the storage of ES cells, they are stored frozen at about −80° C. or below in an appropriate freezing medium (e.g. Dulbecco's modification of Eagle's medium (DMEM) supplemented with 10% DMSO, 10% fetal bovine serum).

[Non-Human Animals Deficient in Expression of LLPL Gene]

The non-human animal deficient in expression of LLPL gene of the invention (hereinafter, sometimes referred to as the "gene expression deficient non-human animal") is an animal created by genetic engineering using, for example, cells derived from the above-described mammal ES cell wherein its LLPL gene is inactivated. One example is a non-human animal wherein an inactivated LLPL gene sequence was introduced into germ cells and somatic cells at an early stage of embryo formation.

As the non-human animal used for this purpose, the same animals as mentioned hereinbefore may be used.

The LLPL gene can be knocked out by introducing the targeting vector described above into non-human animal ES cells or non-human animal ovules according to conventional methods (e.g. electroporation, microinjection, the calcium phosphate method, lipofection, agglutination, the particle gun method, or the DEAE-dextran method) (electroporation is preferable for introduction into ES cells, and microinjection is preferable for introduction into ovules), to thereby homologously recombine the inactivated LLPL gene sequence on the targeting vector with the LLPL gene on the chromosome of the non-human animal ES cells or non-human animal ovules.

Cells in which the LLPL gene is knocked out can be judged by Southern hybridization analysis using as a probe a DNA sequence on the LLPL gene or in the vicinity thereof, or by PCR analysis using as one primer a DNA sequence on the targeting vector and as the other primer a mouse-derived DNA sequence in a region adjacent to but not including the LLPL gene used in the targeting vector.

When non-human animal ES cells were used, those cell clones in which the endogenous LLPL gene has been inactivated by homologous recombination are cloned. The resultant cells are injected into a non-human animal embryo or blastocyst at an appropriate stage embryogenesis, for example at the 8-cell stage (injection method) or an LLPL gene inactivated ES cell mass is sandwiched with two 8-cell stage embryos (collective chimera method). The resulting chimeric embryo is transplanted into the pseudopregnant uterus of the non-human mammal.

The animal thus created is a chimeric animal composed of cells having the normal LLPL locus and cells having the artificially mutated LLPL locus.

When a part of the germ cells of the chimeric animal has the mutated LLPL locus, it is possible to mate such a chimeric individual with a normal individual to thereby obtain offspring individuals, and then select those individuals in which every tissue is composed of cells having the artificially mutated LLPL locus, for example, by judging their coat colors. The thus selected individuals are usually LLPL expression hetero-deficient individuals. LLPL expression homo-deficient individuals can be obtained from offspring individuals produced by mating these LLPL expression hetero-deficient individuals with each other.

When ovules are used, a transgenic non-human mammal wherein a gene of interest has been introduced into its chromosomes can be prepared by injecting a solution of the targeting vector into the ovule nucleus by microinjection. By comparing the resultant transgenic animals, those animals in which a mutation has been introduced into the LLPL locus by homologous recombination can be selected.

The non-human animal deficient in expression of LLPL gene can be discriminated from normal animals by determining the amount of mRNA of the animal by conventional methods and then comparing the expression levels indirectly.

The individuals with the LLPL gene thus knocked out are mated to verify that the animals obtained by mating them with each other also have the LLPL gene knocked out. Then, they can be sub-bred under usual breeding conditions.

Further, preparation and maintenance of the germ line may also be performed in accordance with conventional methods. Briefly, by mating male and female animals both having the inactivated gene sequence, homozygotes having the inactivated gene sequence in both homologous chromosomes can be obtained. The homozygotes thus obtained are bred under such conditions that, with regard to the dam, the number of homozygotes is plural per normal individual. By mating male and female heterozygotes, homozygotes and heterozygotes both having the inactivated gene sequence can be sub-bread. The progeny of those animals having the inactivated gene sequence thus obtained is also included in the non-human animal deficient in expression of LLPL gene of the invention.

[Evaluation of Mammals Deficient in Expression of LLPL Gene]

The non-human animal deficient in expression of LLPL gene of the invention (in particular, LLPL homo-deficient non-human animal, preferably LLPL homo-deficient mouse) has the following characters.

(1) When fed with a high lipid/high cholesterol diet, levels of total cholesterol and LDL+VLDL cholesterol in plasma; triglycerides, phospholipids, free cholesterol and total cholesterol in the liver; and liver weight tend to be lower than the corresponding levels in the corresponding wild-type animals.

(2) When fed with a high lipid/high cholesterol diet, findings of fatty liver such as increase in vacuoles and disturbance of the trabecular structure due to excessive fat accumulation in hepatocytes, increase in single cell necrosis, varied sizes of nuclei and mononuclear cell infiltration are observed in histopathological examination. The degree of these findings is lighter than those observed in the corresponding wild-type animals.

(3) When fed with a high lipid/high cholesterol diet, triglyceride content, phospholipids content and free cholesterol content out of the lipid contents of the liver show significant low values compared to those in the corresponding wild-type animals.

The LLPL/ApoE double-deficient non-human animal (in particular, mouse) of the invention has the following character.

(1) When compared with ApoE deficient animals, the ratio of arteriosclerosis lesions is increased about 2- to 3-fold.

[Disease Model Animals]

Mammal ES cells, which the LLPL gene is inactivated herewith, are very useful in creating non-human animals deficient in expression of LLPL gene. Further, the non-human animals deficient in expression of LLPL gene; disease model animals generated by subjecting the above animals to drug induction or by loading stress on the animals; better disease model animals generated by mating the non-human animal deficient in expression of LLPL gene with other disease model animal; disease model animals generated by subjecting the disease model animal generated by mating the non-human animal deficient in expression of LLPL gene with other disease model animal to drug induction or by loading stress on the disease model animal; bone marrow-transplanted animal obtained by using the non-human animal deficient in expression of LLPL gene and other disease model animal; or tissues thereof; or cells derived from such animals or tissues can be better model systems for diseases resulting from deficiency of LLPL (e.g. arteriosclerosis, hypercholesterolemia, hyperglyceridemia, hyperlipemia, diabetic complication, diabetic nephropathy, diabetic neuropathy, diabetic retinopathy, insulin-dependent diabetes, hepatopathy, hypoadrenalism, senile pancreatic hypofunction, etc.; preferably, arteriosclerosis). They therefore are useful in elucidating the causes of these diseases and examining therapeutic method for such diseases. Specific examples of other disease models useful in the invention include arteriosclerosis model nice such as LDL receptor-deficient mouse or ApoE-deficient mouse, CETP-transferred mouse, ApoB-transferred mouse, etc. or mice obtainable by mating these mice; type II diabetes model mice comprising impaired glucose tolerance and/or insulin resistance (KK mouse, KKA$^y$ mouse, ob/ob mouse, db/db mouse, IRS-1 deficient mouse, IRS-2 deficient mouse, glucokinase deficient mouse or mice obtainable by mating them) and type I diabetes model mice (such as NOD mouse). Model mice created by bone marrow transplantation wherein the deficiency or rise in gene expression is localized to the blood system may also be enumerated [Linton, M. F. et al., Science 267:1034-1037 (1995)] also included. The bone marrow-transplanted mice have a latent possibility to become a more suitable disease model because of the limitation of the site of mutated gene functions. For example, the following mice are also included in the bone marrow-transplanted mice: a mouse created by using as a donor animal a disease model animal obtained from the above-mentioned non-human animal deficient in expression of LLPL gene, collecting its bone marrow, and transplanting the bone marrow to a recipient animal whose bone marrow was destroyed by radioactive irradiation in advance, or a mouse created by using other disease model as a donor animal, collecting its bone marrow, and transplanting the bone marrow to a recipient animal that is a disease model animal obtained from the non-human animal deficient in expression of LLPL gene whose bone marrow was destroyed by radioactive irradiation in advance. Taking arteriosclerosis as an example, macrophages, etc. infiltrating into lesions do not express LLPL in the former; and macrophages, etc. infiltrating into lesions alone express LLPL in the latter.

According to a preferable embodiment of the invention, examples of other disease model animals to be mated with the non-human animal deficient in expression of LLPL gene include an animal deficient in ApoE gene which is associated with arteriosclerosis. The double-function deficient model animal created by mating the non-human animal deficient in expression of LLPL gene of the invention with an arteriosclerosis disease model animal is useful in elucidating relationships with diseases attributable to the arteriosclerosis-related gene ApoE, screening for prophylactic and/or therapeutic drug for various diseases resulting from LLPL deficiency and ApoE deficiency, elucidating the causes of LLPL- and ApoE-related diseases and examining therapeutic methods for such diseases.

Thus, it is possible to use the non-human animals deficient in expression of LLPL gene; disease model animals generated by subjecting the above animals to drug induction or by loading stress on the animals; disease model animals generated by mating the non-human animal deficient in expression of LLPL gene with other disease model animal; disease model animals generated by subjecting the disease model animal generated by mating the non-human animal deficient in expression of LLPL gene with other disease model animal to drug induction or by loading stress on the disease model animal; disease model animals created by using a disease model animal obtained from the non-human animal deficient in expression of LLPL gene and other disease model animal and performing bone marrow transplantation between them; or tissues thereof; or cells derived from such animals or tissues, for screening for prophylactic and/or therapeutic drug for above-mentioned diseases. The above-mentioned tissues or cells derived therefrom may be used for the screening, for example, in such a manner that a specific activity is measured using a homogenate of liver or kidney, or that the activity or yield of a specific product is measured.

[The Screening Method of the Invention]

The non-human animals deficient in expression of LLPL gene; disease model animals generated by subjecting the above animals to drug induction or by loading stress on the animals; disease model animals generated by mating the non-human animal deficient in expression of LLPL gene with other disease model animal; disease model animals generated by subjecting the disease model animal generated by mating the non-human animal deficient in expression of LLPL gene with other disease model animal to drug induction or by loading stress on the disease model animal; disease model animals created by using a disease model animal obtained from the non-human animal deficient in expression of LLPL gene and other disease model animal and performing bone marrow transplantation between them; or tissues thereof; or cells derived from such animals or tissues useful in the screening method of the invention are the same as those described above.

Examples of the test compound include peptides, proteins, non-peptidic compounds, synthetic compounds, fermentation products, cell extracts, plant extracts, and animal tissue extracts. These compounds may be novel compounds or known compounds.

Specifically, the non-human animals deficient in expression of LLPL gene of the invention; disease model animals generated by subjecting the above animals to drug induction or by loading stress on the animals; disease model animals generated by mating the non-human animal deficient in expression of LLPL gene with other disease model animal; disease model animals generated by subjecting the disease model animal generated by mating the non-human animal deficient in expression of LLPL gene with other disease model animal to drug induction or by loading stress on the disease model animal; disease model animals created by using a disease model animal obtained from the non-human animal deficient in expression of LLPL gene and other disease model animal and performing bone marrow transplantation between them (hereinafter, sometimes these may be referred to as the "LLPL gene expression deficient non-human animals, etc."); or tissues thereof; or cells derived from such animals or tissues are treated with a test compound, and then compared with non-treated control animals. Prophylactic and/or therapeutic effects of the test compound can be tested by using, as indicators, changes in individual organs, tissues, cells or symptoms of the relevant disease of the test animals.

As a method of treating the test animals (LLPL gene expression deficient non-human animals, etc.) with a test compound, oral administration, intravenous injection or the like may be used. Such a method may be appropriately selected depending on the condition of the test animals, the nature of the test compound, etc. The dose of the test compound may be appropriately selected depending on the administration route, the nature of the test compound, etc.

For example, when prophylactic and/or therapeutic drug for arteriosclerosis or hyperlipemia are screened for, cholesterol loading treatment is given to the LLPL gene expression deficient non-human animals, etc. of the invention. Test compounds are administered before or after the cholesterol loading treatment, and then blood cholesterol levels, body weight changes, etc. are measured with the passage of time. Thus, screening can be performed. When prophylactic and/or therapeutic drug for type I diabetes are screened for, a drug such as STZ or alloxan is administered to the LLPL gene expression deficient non-human animals, etc. of the invention. Then, test compounds are administered before or after glucose loading treatment, and blood glucose levels, body weight changes, etc. are measured with the passage of time. Thus, screening can be carried out.

[Prophylactic and/or Therapeutic Drug Obtainable by the Screening Method of the Invention]

The prophylactic and/or therapeutic drug obtainable by the screening method of the invention contains a compound selected from the above-described test compounds, has prophylactic and/or therapeutic effect upon a disease resulting from LLPL deficiency, and is useful as a medicine, such as a prophylactic and/or therapeutic drug for a disease resulting from LLPL deficiency that is safe and of low toxicity. Compounds derived from such a selected compound may also be used in a similar manner.

The compound obtained by the above screening method may be in a salt form. Examples of such salts include pharmaceutically acceptable salts, such as salts formed with inorganic bases, salts formed with organic bases, salts formed with inorganic acids, salts formed with organic acids, and salts formed with basic or acidic amino acids.

Preferable examples of salts formed with inorganic bases include alkali metal salts such as sodium salts and potassium salts; alkaline earth metal salts such as calcium salts, magnesium salts; aluminium salts and ammonium salts.

Preferable examples of salts formed with organic bases include salts formed with trimethylamine, trimethylamine, pyridine, picoline, 2,6-lutidine, ethanolamine, diethanolamine, triethanolamine, cyclohexylamine, dicyclohexylamine or N,N'-dibenzylethylenediamine.

Preferable examples of salts formed with inorganic acids include salts formed with hydrochloric acid, hydrobromic acid, sulfuric acid or phosphoric acid.

Preferable examples of salts formed with organic acids include salts formed with formic acid, acetic acid, propionic acid, fumaric acid, oxalic acid, maleic acid, citric acid, succinic acid, malic acid, methanesulfonic acid, benzenesulfonic acid or benzoic acid.

Preferable examples of salts formed with basic amino acids include salts formed with arginine, lysine or ornithine; and preferable examples of salts formed with acidic amino acids include salts formed with aspartic acid or glutamic acid.

When the compounds, or salts thereof, obtainable by the screening method of the invention are used as the above-described therapeutic drug and/or prophylactic, they may be used by conventional means. For example, the compound or a salt thereof may be used orally in the form of tablets (sugar-coated, if necessary), capsules, elixirs, microcapsules or the like; or parenterally in the form of injections such as aseptic solutions or suspensions in water or other pharmaceutically acceptable liquids. These preparations may be produced, for example, by mixing the compound or a salt thereof with physiologically acceptable carriers, flavoring agents, excipients, vehicles, antiseptics, stabilizers, binders, etc. in unit dosage forms required for preparing generally approved pharmaceutical preparations. The amounts of active ingredients in these formulations are selected so that an appropriate dose within the specified range can be obtained.

Examples of additives which may be mixed in tablets, capsules, etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is capsule, liquid carrier such as oils and fats may further be included in addition to the above-mentioned materials. Sterile compositions for injection can be formulated according to conventional practices in pharmaceutical manufacturing, e.g., by dissolving or suspending active ingredients, naturally occurring vegetable oils such as sesame oil, coconut oil, etc. in vehicles such as water for injection.

Examples of aqueous liquids for injection include physiological saline and isotonic solutions containing glucose and other auxiliary agents (e.g. D-sorbitol, D-mannitol, sodium chloride, etc.). They may be used in combination with a suitable auxiliary solubilizer such as alcohol (e.g. ethanol, etc.), polyalcohol (e.g. propylene glycol, polyethylene glycol, etc.), nonionic surfactant (e.g. Polysorbate 80™, HCO-50, etc.). Examples of oily liquids include sesame oil, soybean oil, etc. They may be used in combination with an auxiliary solubilizer such as benzyl benzoate, benzyl alcohol, etc. In addition, buffers (e.g. phosphate buffer, sodium acetate buffer, etc.), analgesic agents (e.g. benzalkonium chloride, procaine hydrochloride, etc.), stabilizers (e.g. human serum albumin, polyethylene glycol, etc.), preservatives (e.g. benzyl alcohol, phenol, etc.), antioxidants, etc. may also be admixed therewith. Usually, the prepared injections are filled in appropriate ampoules.

Since the thus obtained preparations are safe and low-toxic, they can be administered to human or other warm-blooded animals (e.g., mouse, rat, rabbit, sheep, pig, bovine, horse, bird, cat, dog, monkey, chimpanzee, etc.).

Dose levels of the compound or a salt thereof may vary depending upon conditions of the patient, etc. In the case of oral administration, generally, the compound or a salt thereof is administered to adult arteriosclerosis patients (body weight: 60 kg) at a dose of about 0.1 to 100 mg/day, preferably about 1.0 to 50 mg/day, more preferably about 1.0 to 20 mg/day. With respect to parenteral administration, the dose per administration varies depending on the patient, target organ, conditions, route of administration, etc. When the compound or a salt thereof is administered to adult arteriosclerosis patients (body weight: 60 kg) in the form of an injection, it is convenient to inject intravenously at a dose of about 0.01-30 mg/day, preferably about 0.1-20 mg/day, and more preferably about 0.1-20 mg/day. For other animals, corresponding doses may be administered after conversion of the above-mentioned values per 60 kg based on actual body weights.

In the specification and drawings of the present application, the abbreviations used for bases (nucleotides), amino acids and so forth are those recommended by the IUPAC-IUB Commission on Biochemical Nomenclature or those conventionally used in the art. Examples of such abbreviations are given below. Amino acids that may have optical isomers are intended to represent their L-isomer unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan Pro: Proline
Asn: Asparagine
Gln: Glutamine The SEQ ID NOS of the SEQUENCE LISTING of the present specification represent the sequences as indicated below.

[SEQ ID NO: 1]
This shows the amino acid sequence for a mouse-derived LLPL.

[SEQ ID NO: 2]
This shows the nucleotide sequence of a DNA encoding the mouse-derived LLPL.

[SEQ ID NO: 3]
This shows the nucleotide sequence of primer P94-1.

[SEQ ID NO: 4]
This shows the nucleotide sequence of primer P101-4.

[SEQ ID NO: 5]
This shows the nucleotide sequence of primer SI-75.

[SEQ ID NO: 6]
This shows the nucleotide sequence of primer P3-t.

[SEQ ID NO: 7]
This shows the nucleotide sequence of primer P4-s.

EXAMPLES

Hereinbelow, the present invention will be described more specifically with reference to the following Reference Examples and Examples. However, the present invention is not limited to these examples.

Reference Example 1

Cultivation of ES Cells

129/SvEv-derived AB2.2-Prime ES cells (Lexicon) were cultured based on the method of Joyner et al. (Gene Targeting: A Practical Approach, 1993, Oxford University Press, or its translated version Gene Targeting, compiled under the supervision of Tetsuo Noda and published by Medical Science International). ES cells and feeder cells were cultured using the recommended ESQ DMEM medium (medium for ES cells) containing 15% FBS, 2 mM L-glutamine, $10^{-4}$ M β-mercaptoethanol, 50 U/ml penicillin and 50 μg/ml streptomycin, at 37° C. under 5% $CO_2$. ES cells were cultured on a layer of feeder cells which had been arrested by culturing in a medium containing 10 μg/ml mitomycin C (Sigma) for 3 hr. In order to inhibit the differentiation of ES cells as much as possible, medium exchange was performed basically in a half volume and cells were sub-cultured in every two to three days.

Reference Example 2

Screening of Mouse Genomic DNA Library

Plasmid pCMV-SPORT (pTB2010) comprising mLLPL (mouse LLPL) cDNA was digested with restriction enzyme SmaI to thereby isolate an approx. 1 kbp fragment spanning from the vector's MCS (multi-cloning site) located at the N-terminal to the SmaI site of the mLLPL. Using this fragment as probe A, three clones of plasmid mLLPL/pBeloBacll comprising the full-length genomic sequence of mLLPL were obtained from 129/Svj mouse genomic library using BAC ES Mouse Hybridization Library Screening Services (Genome Systems). These three clones were fragmented by treatment with restriction enzymes EcoRI and PstI to prepare DNA hybridization fragments, which were then analyzed by Southern hybridization using a DNA probe comprising almost the entire region mLLPL ORF (open reading frame). The DNA probe was prepared by PCR using pTB2010 as a template, a sense-strand primer P94-1 [5'-GGT AAC CAG TTG GAA GCA AAG-3'; 21 mers (SEQ ID NO:3)] and an antisense-strand primer P101-4 [5'-CCC CGG GTG GCG TCA T-3'; 16 mers (SEQ ID NO:4)]. Two DNA fragments of approx. 11 kbp and 7.5 kbp were obtained as positive bands from the EcoRI digest; and three DNA fragments of approx. 6.5 kbp, 1.5 kbp and 0.6 kbp were obtained from the PstI digest. Thus, five positive bands of mLLPL were detected.

These fragments were individually subcloned into pUC118 vector to prepare plasmids EcoRI (11 kbp)/pUC118, EcoRI (7.5 kbp)/pUC118, PstI (6.5 kbp)/pUC118, PstI (1.5 kbp)/pUC118 and PstI (0.6 kbp)/pUC118. These plasmids were analyzed by restriction enzyme mapping and their nucleotide sequences were determined. The results revealed that the clones obtained above encompass the entire region (approx. 13 kbp) of the genomic fragment of mLLPL; the exon-intron structure on the 13 kbp mLLPL genomic fragment was determined (FIG. 1). It has become clear that the ORF of mouse LLPL are composed of a total of six exons, and that the lipase motif (expected to be the active site) exists on the 5th exon.

Reference Example 3

Construction of Targeting Vector pTB2224

Figure 2:
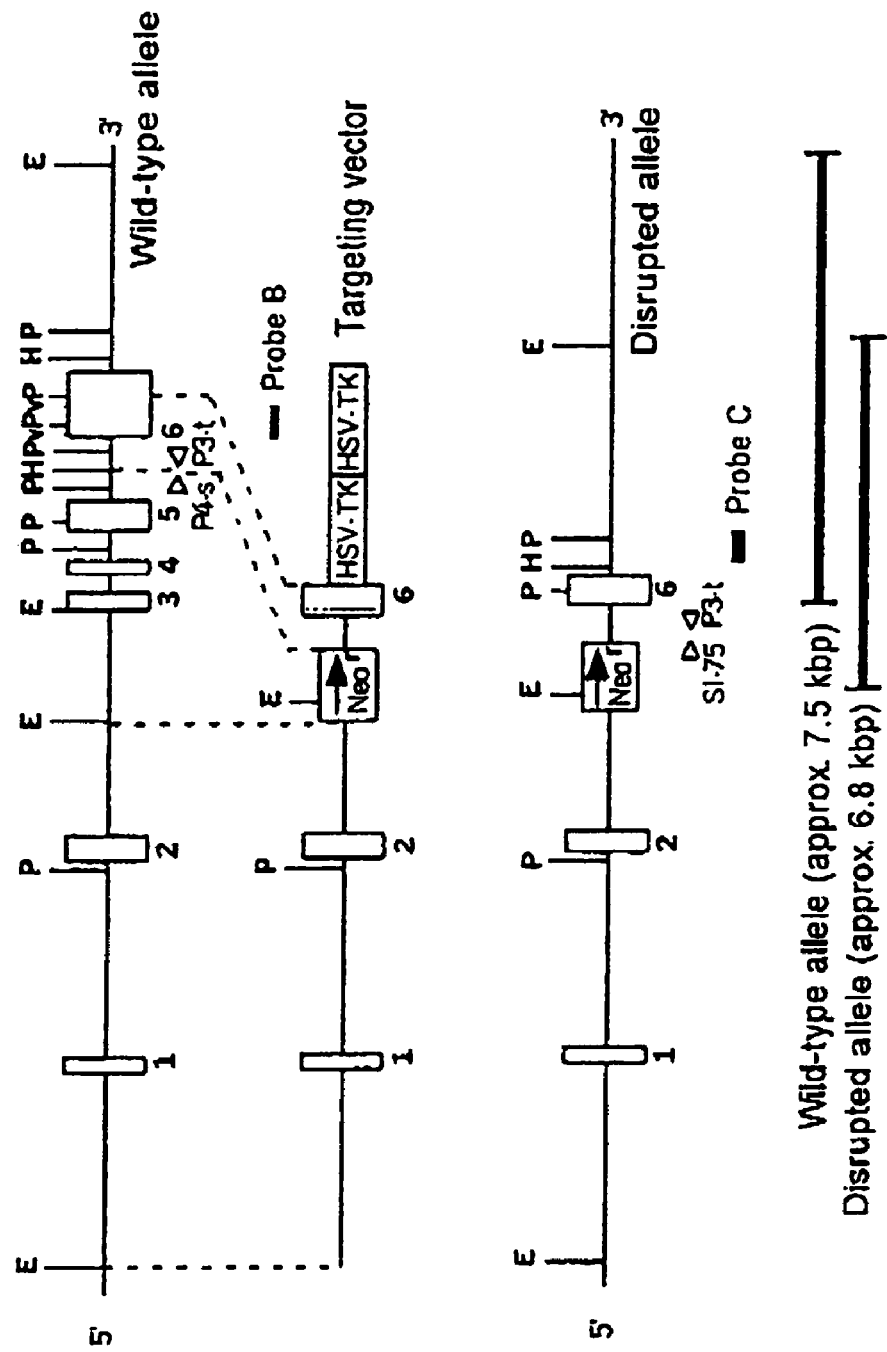
FIG. 2 shows a construction drawing of the targeting vector obtained in Reference Example 3. In this Figure, Neo$^r$ represents neomycin resistance gene, and HSV-TK represents herpes simplex virus thymidine kinase gene.

Using the plasmids obtained by digesting mLLPL/pBelo-Bacll with restriction enzymes and subcloning into pUC118 vector, DNA fragments to be a short arm and a long arm were prepared. The following operations were carried out in order to prepare a short arm consisting of a HindIII/PstI fragment containing the 6th exon (1.1 kbp) to which SalI site is added at both ends, and a long arm consisting of an EcoRI fragment containing the 1st and 2nd exons (11 kbp) to which NotI site is added at both ends. Briefly, a HindIII fragment (1.3 kbp) was isolated from EcoRI (7.5 kbp)/pUC118 plasmid and cloned into the HindIII site of pBluescriptII. From the resultant clones, a clone was selected in which the 5' end of the insert of the MCS is located near the SalI site. This plasmid was digested with BamHI and blunt-ended with T4 DNA polymerase to thereby obtain a plasmid into which a SalI linker is inserted. The resultant plasmid was digested with PstI and self-ligated to thereby remove a PstI fragment (0.2 kbp) located at the 3' end of the insert The resultant plasmid was digested with SalI to thereby obtain a DNA fragment having a SalI site added at both ends that was to be the short arm. On the other hand, a DNA fragment to be the long arm was obtained as follows: an EcoRI fragment (11 kbp) was cloned into the EcoRI site of pGEM-T Easy vector (Promega), and the resultant plasmid was digested with NotI to thereby obtain a DNA fragment to which a NotI site is added at both ends. The thus prepared short arm and long arm were ligated to the XhoI site and the NotI site, respectively, of pPolIIshort-neobPA-HSVTK vector (Ishibashi, S. et al., J. Clin. Invest. 1994; 93 (5): 1885-93) to thereby obtain a targeting vector of interest, pTB2224 (FIG. 2).

Example 1

Selection of LLPL Gene Deficient ES Cells

Figure 3:
FIG. 3 shows the results of Southern hybridization of the LLPL-knockout ES cell clones obtained in Example 1. Gene-transferred ES cell clones: IX-1-5 (lane 1); LX-1-8 (lane 2); LX-2-3 (lane 3); LX-2-80 (lane 4); LX-2-163 (lane 5); and wild-type ES cell clones (lanes 6, 7); STO cells (lane 8).

The ES cells obtained in Reference Example 1 which had been grown to almost confluency were treated with trypsin as described below three hours after medium exchange to thereby prepare an ES cell suspension. Briefly, the ES cells were washed with 10 ml of PBS/EDTA three times and suspended in 3 ml of 0.25% trypsin/1 mM EDTA solution (GibcoBRL). Then, 7 ml of D-PBS (−) was added thereto to suspend cells. The resultant suspension was centrifuged to harvest cells. The harvested cells were washed with 10 ml of D-PBS (−) three times and then resuspended in 1 ml of D-PBS (−) to prepare an ES cell suspension. The targeting vector DNA (approx. 120 μg) pTB2224 obtained in Reference Example 3 was linearized with restriction enzyme SalI and then subjected to phenol/chloroform extraction and ethanol precipitation. After purification, the precipitate was dissolved in 100 μl of Milli-Q water. To this DNA solution, 0.9 ml of D-PBS (−) was added to make a 1 ml solution, which was then added to the ES cell suspension prepared above. The cell suspension was left for 3 min. Then, the cell suspension was dispensed into electroporation cuvettes (1 ml/cuvette), and electroporation into ES cells was performed using Cell Porator Electroporation System I (Gibco BRL). (The system is set at "Charge". After confirmation of 330 μF and Low Q, the monitor value is raised to about 300 with Fast-UP. Then, the system is set at "Amp". When the monitor value is decreased to 275 with Med-Down, "Trigger" is pushed immediately.) The cells which had undergone electroporation were transferred into 40 ml of ES cell medium, stirred gently and then plated on feeder cells which had been arrested in four 10 cm dishes. Twenty-four hours after the plating, G418 (final concentration: 190 u g/ml; Gibco BRL) was added to the medium. Four days after the electroporation, 1-(2-deoxy-2-fluoro-β-D-arabinofuranosyl)-5-iodouracil (FIAU; final concentration 100 ng/ml) was added to perform selective cultivation of LLPL gene deficient ES cells. The medium was exchanged everyday. Those colonies grown from day 9 to day 11 were collected, and clones of interest were selected by the primary screening (Southern analysis of PCR products) and the secondary screening (genomic Southern screening). Whether or not the resultant G418 resistant clones are deficient in LLPL gene was judged as follows: a PCR was performed using as a template a cell lysate prepared from a part of each colony collected, a sense-strand primer PI-75 (SEQ ID NO: 5) on the neomycin resistance gene and an antisense-strand primer P3-t (SEQ ID NO: 6) located on the short arm. The resultant PCR product was electrophoresed on agarose gel, followed by alkali transfer onto Hybond N+ (Amersham Pharmacia Biotech). The Southern blots prepared were analyzed by Southern hybridization using a 0.4 kbp PvuII fragment in the short arm region as probe B. Those clones in which a 1.2 kbp band had been detected were cultured further in a larger scale, and genomic DNA was extracted from the resultant cells and digested with restriction enzyme EcoRI. The resultant DNA was subjected to genomic Southern analysis using as probe C a 0.5 kbp HindIII/PstI fragment outside of the short arm which is present in the 3' non-translated region of LLPL cDNA. In LLPL gene-knocked out cell clones, bands were detected at 6.8 kbp (disrupted allele) and 7.5 kbp (wild-type allele). In contrast, a band of 7.5 kbp (wild-type allele) alone was detected in wild-type clones (control). Those clones in which both the wild-type allele-derived 7.5 kbp band and the disrupted allele-derived 6.8 kbp band had been detected were finally selected as homologous recombinants of interest. Two experiments were performed to obtain homologous recombinants. The results confirmed that, of the total 430 clones which showed resistance to both G418 and FIAU, 5 clones were homologous recombinants into which the mutation was introduced (FIG. 3).

Example 2

Creation of Chimeric Mice Using Homologous Recombinant ES Cell LX-2-163 Clone

1. The Obtaining of Blastocysts

Animals to obtain blastocysts therefrom were created as described below. First, 8 week-old female C57BL/6 mice (Crj) were purchased and conditioned for one week in SPF animal breeding facilities controlled at 25±1° C. in room temperature, 50±10% in humidity and under 12-hr (from 7:00 to 19:00) lighting conditions. On day 1 of the experiment, more than 10-week old male mice of the same strain were allowed to live with the female mice to allow natural mating. On the next day, the presence of a vaginal plug was examined in the female mice. Those female mice in which the presence of a vaginal plug had been confirmed were bred for another three days until the microinjection experiment.

On the day of the microinjection experiment, the mice were slaughtered by cervical dislocation. The belly was opened, followed by removal of the ovary, the oviduct and the uterus. The portion over the uterine horn was removed. The remaining uterus was separated into a right and left portions. Further, 25G injection needles were inserted from the uterine horn side and the vaginal side, respectively, to perfuse a medium for egg collection (DMEM containing 10% FCS, 100 U penicillin and 100 U streptomycin) into the uterus. The perfusion solution for each uterus was recovered individually into a 3.5 cm petri dish and left stationary in an incubator at 37° C. under 7% $CO_2$ for 30 min or more. Then, blastocysts alone were recovered.

2. Preparation of Homologous Recombinant ES Cells.

Homologous recombinant ES cells frozen at a cell density of $5 \times 10^5$ or $1 \times 10^6$ were thawed on day 2 of the experiment and immediately plated on 6 cm feeder dishes in which STO cells had been cultured in a feeder medium (DMEM containing 10% FCS, 200 mM L-glutamine, 10 mM NEAA, 100 U penicillin and 100 U streptomycin). Then, the ES cells were cultured in an ES medium (DMEM containing 16% FCS, 200 mM L-glutamine, 10 mM NEAA, 100 U penicillin, 100 U streptomycin, 1 M HEPES, 1000 U ESGRO and 0.1 mM β-mercaptoethanol) in an incubator controlled at 37° C. under 7% $CO_2$ for three days until the day of the microinjection experiment.

After removal of the medium, the expanded homologous recombinant ES cells were washed with PBS solution twice. The washed cells were treated with 0.25% trypsin solution for 5 min. After addition of the above-described ES medium, the cells were centrifuged at 1200 rpm for 2 min at 4° C. Subsequently, the supernatant was removed, and 2-3 ml of the ES medium was added to the cells to loosen them. Then, the ES medium was added further to make the volume 10 ml. The resultant cell suspension was plated in a 10 cm culture dish and cultured for 30 min in an incubator controlled at 37° C. under 7% $CO_2$ to thereby allow feeder cells to adhere onto the culture dish. Further, ES cells alone were recovered from the supernatant, placed in a 6 cm petri dish and stored at 4° C. until the start of the microinjection experiment.

3. Microinjection Experiment Using Homologous Recombinant ES Cells

One drop of a microinjection medium (DMEM containing 16% FCS, 200 mM L-glutamine, 10 mM NEAA, 100 U penicillin, 100 U streptomycin, 20 mM HEPES and 0.1 mM β-mercaptoethanol) was applied to the center of the lid of a 6 cm petri dish as an injection chamber. Then, 5 to 10 blastocysts were transferred to the center of the drop, and the above-described homologous recombinant ES cells were transferred to the peripheral part within the drop. Liquid paraffin was added so that the drop did not get dry. Then, the drop was stored cool at 4° C. for 20-30 min. The microinjection experiment was performed based on the method of Hogan et al. (Hogan, B., Costanitini, F., and Lacy, E. (Eds), 1986, Manipulation the mouse embryo: A laboratory manual, New York, Cold Spring Harbor Laboratory Press). The microinjection of homologous recombinant ES cells into blastocysts was performed in a method in which 10-15 ES cells in the drop were collected with a microinjection pipette, and then the pipette was inserted into the blastocyst from the opposite side to the internal cell mass to thereby inject the cells into the blastocoels. The blastocyst which underwent microinjection was transferred into 10% FCS-added DMEM medium and cultured in an incubator controlled at 37° C. under 7% $CO_2$ until the original shape of the blastocyst was restored. Eight to ten normal blastocysts were transplanted into the left and right uterine horns, respectively, of the ICR (JcL) pseudo-pregnant female mice prepared as described below. Then, the mice were bred in breeding chambers controlled at 25±1° C. in room temperature, 50±10% in humidity and under 12-hr (from 7:00 to 19:00) lighting conditions.

Pseudo-pregnant mice were created as follows. Eight-week-old ICR (JcL) female mice were purchased and conditioned for one week in SPF animal breeding facilities controlled at 25±1° C. in room temperature, 50±10% in humidity and under 12-hr (from 7:00 to 19:00) lighting conditions. On day 2 of the experiment, more than 10-week old vasoligated ICR (JcL) male mice prepared in advance were allowed to live with the female mice to allow natural mating. On the next day, the presence of a vaginal plug was examined in the female mice. Those female mice in which the presence of a vaginal plug was confirmed were bread further for 2 days and then supplied to the microinjection experiment.

As a result, 49 offspring mice were obtained in the microinjection experiment using IX-2-163 clone. Of the 49 individuals, 27 individuals were chimeric mice with agouti coat color. The contribution ratio of ES cells to the coat color of a chimeric mouse (chimeric ratio) exhibited variance among individuals. In this experiment, 10 male chimeric mice were obtained which had high chimeric ratios exceeding 75%.

Example 3

Creation of LLPL Deficient Mice

Those male mice showing high chimeric ratios alone were mated with more than 10-week old female C57BL/6 (Crj) mice. Initially, the judgment of the shift of ES cells to a germ line was made by confirming the coat colors of offspring mice. All of the 75 offspring mice obtained from mating with chimeric mice in which the contribution ratios of LX-2-163 clone cells were almost 100% exhibited agouti coat color; thus, it was believed that all the offspring mice were derived from the ES cells. In the 120 offspring mice obtained from mating with male chimeric mice having chimeric ratios higher than 75%, 80 individuals exhibited agouti coat color derived from the ES cells. Subsequently, for those mice exhibiting agouti coat color, gene deficiency was judged by PCR and Southern analysis as described below.

DNA was extracted from the tail vein of each of ES cell-derived offspring mice by conventional methods. A PCR was performed using the resultant DNA as a template and the following three primers: a sense-strand primer PI-75 [5'-GAT TGG GAA GAC AAT AGC AGG CAT GC-3'; 26-mers (SEQ ID NO: 5)] on the neomycin resistance gene, a sense-strand prime P4-s [5'-CGC TCA TCT GAT CAT CGT AAT GAT CG-3'; 26-mers (SEQ ID NO: 7)] on the LLPL gene and an antisense-strand primer P3-t [5'-TGG TGC AAG TAT TAT CAC CGC CCA TT-3'; 26-mers (SEQ ID NO: 6)] located on the short arm. The PCR product was analyzed on agarose gel. With these primers, a 0.4 kbp band is detected from the wild-type allele in which no mutation is introduced; and a 0.3 kbp band is detected from the disrupted allele in which the mutation was introduced into the LLPL gene. Of 28 offspring mice (male: 12, female: 16) obtained from the mating of chimeric mice (F0) with C57B/6J mice, 16 mice (male: 6, female: 10) exhibited amplification of the two bands of 0.3 kbp and 0.4 kbp. They were believed to the heterozygous mice in which the mutation (deficiency) was introduced into the LLPL gene. The DNA from each of these mice was digested with EcoRI and analyzed by genomic Southern hybridization using probe C in the same manner as in Example 1. As a result, two bands were detected at 7.5 kbp and 6.8 kbp as they were detected in the LLPL gene deficient ES cell clone LX-2-163 obtained in Example 1. Thus, it was confirmed that they were heterozygous mice (F1).

Example 4

Characters of LLPL Deficient Mice

Figure 4:
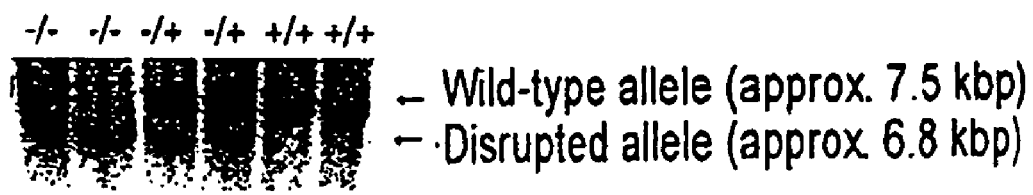
FIG. 4 shows the results of Southern hybridization of the LLPL deficient mice (F2) obtained in Example 4.

By mating the LLPL hetero-deficient male and female mice (F1) obtained in Example 3, LLPL homo-deficient mice (F2) were obtained with a probability almost according to Mendel's law. FIG. 4 shows the results of analysis using Southern hybridization in the same manner as in Example 3. In LLPL homo-deficient mice, the 6.8 kbp band alone was detected (FIG. 4).

Figure 5:
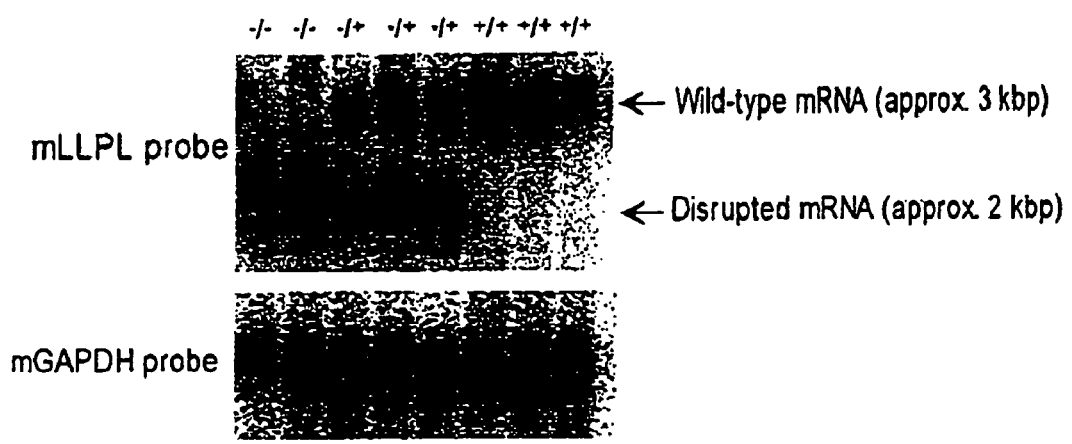
FIG. 5 shows the results of Northern blot analysis of the LLPL expression in peritoneal macrophages in the LLPL deficient mice obtained in Example 4. In this Figure, +/+ represents wild-type mice; +/− represents hetero-deficient mice; and −/− represents homo-deficient mice.

Further, 1.5 ml of thioglycollate was injected intraperitoneally into male F2 mice. Four days thereafter, the mice were slaughtered by cervical dislocation, and the peritoneal macrophages were recovered in a form of suspension in 10 ml of D-PBS(-). Poly(A)$^+$ RNA was purified from the resultant macrophage and subjected to Northern blot analysis using as a probe a 0.5 kbp DNA fragment located in an N-terminal region of the LLPL ORF. The results are shown in FIG. 5. In wild-type mice (LLPL$^{+/+}$), a 3 kbp band derived from the endogenous LLPL gene was observed. In hetero-deficient mice (LLPL$^{+/-}$), a 3 kbp band and a 2 kbp band corresponding to the active site-deficient LLPL gene were observed. In homo-deficient mice (LLPL$^{-/-}$), a 2 kbp band alone corresponding to the active site-deficient LLPL gene was detected. Thus, it was confirmed at the mRNA level that expression of a short mRNA representing the active site-deficient LLPL gene is observed in LLPL homo-deficient mice (FIG. 5).

Figure 6:
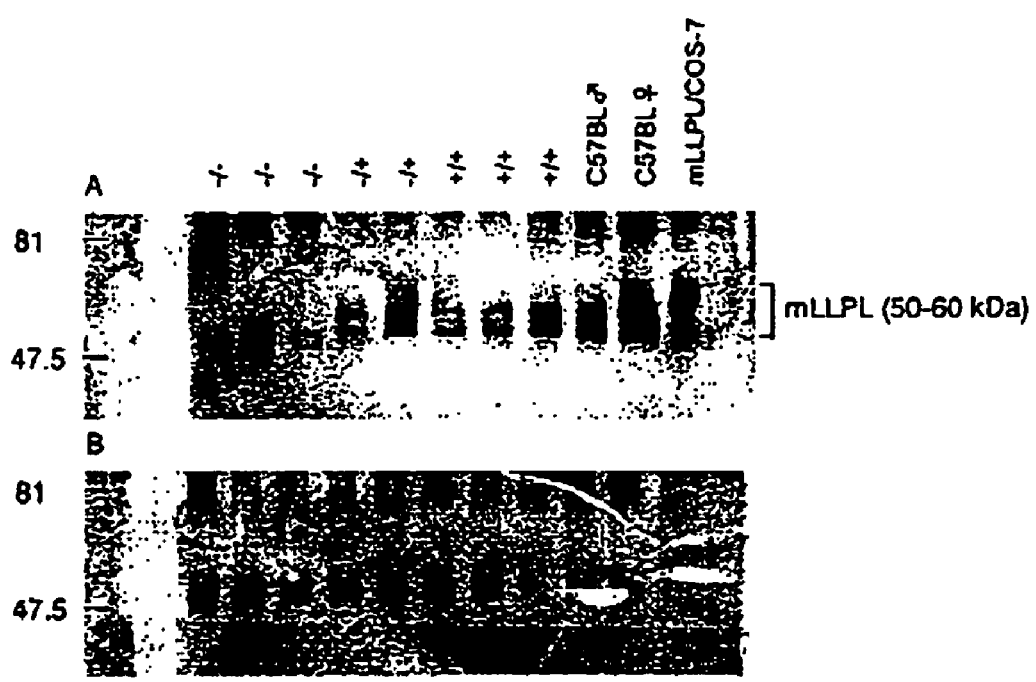
FIG. 6 shows the results of Western blot analysis of the LLPL produced in the culture supernatant of peritoneal macrophages of the LLPL deficient mice obtained in Example 4; the LLPL was immunoprecipitated prior to Western blot analysis. In this Figure, +/+ represents wild-type mice; +/− represents hetero-deficient mice; and −/− represents homo-deficient mice.
Figure 9:
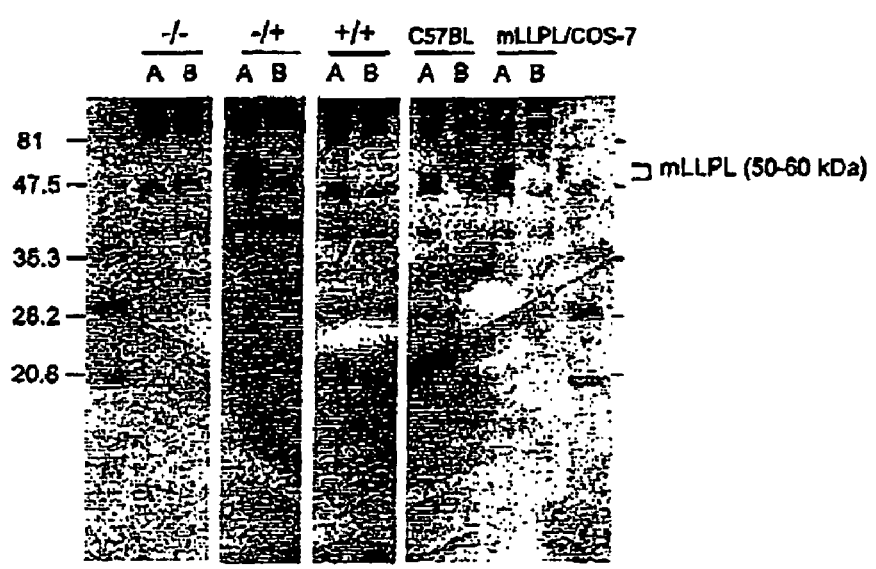
FIG. 9 shows the results of Western blot analysis (using Multi-gel 12.5) of the LLPL produced in the culture supernatant of peritoneal macrophages of the LLPL deficient mice obtained in Example 4; the LLPL was immunoprecipitated prior to Western blot analysis. In this Figure, +/+ represents wild-type mice; +/− represents hetero-deficient mice; and −/− represents homo-deficient mice.

Peritoneal macrophages obtained in the same manner as described above were cultured in DMEM (10% FBS) overnight to allow the cells to adhere to a 10 cm dish. Then, the medium was replaced with 5 ml of serum-free DMEM, and the cells were cultured for 5 days. The culture supernatant was recovered and sterilized with a 0.22 μm filter. The mLLPL protein in the thus obtained supernatant sample was immunoprecipitated. Briefly, 10 μl of 10% SDS was added to 900 μl of the culture supernatant sample, which was then heated at 100° C. for 2 min to denature the protein. To the resultant sample, a 100 μl solution containing 20 mM Tris-HCl (pH 7.4), 150 mM NaCl, 10% Triton-X-100 and 0.1% $NaN_3$ and 10 μg of polyclonal antibody PCL02 to hLLPL protein that cross-reacts with mLLPL protein or rabbit IgG were added. The mixture was rotated in a 1.5 ml Eppendorf tube at 4° C. overnight. Further, 50 μl of anti-rabbit IgG agarose (1:1 slurry) (Sigma) was added thereto, and the resultant mixture was rotated in a 1.5 ml Eppendorf tube at 4° C. overnight. The agarose gel after immunoprecipitation was washed with a solution containing 20 mM Tris-HCl (pH 7.4), 150 mM NaCl, 1% Triton-X-100, 1 mg/ml BSA and 0.1% NaN$_3$ three times, and then washed with TBS once and with 50 mM Tris-HCl (ph 7.4) once. After washing, the protein was eluted into 40 µl of 2×Laemmli sample buffer (Bio-Rad) and heated at 100° C. for 5 min for denaturation. Then, 20 µl of the resultant sample was subjected to SDS-PAGE. Electrophoresis was performed by conventional methods, followed by Western blotting to a Hybond-P membrane (Amersham Pharmacia Biotech). Then, Western analysis was performed using biotinylated PCL02 antibody as a primary antibody and streptavidin AP-conjugate (Boehringer Manheim) as a secondary antibody. Mouse LLPL protein showed a broad band at around 50 kDa, but when degraded it showed a plurality of bands in a region slightly less than 50 kDa. In order to detect the wild-type LLPL protein (approx. 50 kDa) and the variant LLPL protein lacking the active site whose expression was confirmed at the mRNA level (if this is produced as a protein, the size is expected to be approx. 15 kDa), Western analysis was performed using Multi-gel 12.5 and Multi-gel 15/25 (both from Daiichi Kagaku) which are different in protein fractionation range. FIG. 9 shows the results of Western blot analysis using Multi-gel 12.5. In hetero-deficient mice and wild-type mice, the LLPL protein (a band around 50-60 kDa) produced was detected. However, no band was detected around 50 kDa in homo-deficient mice. Even when Multi-gel 15/25 was used, no band which is believed to be derived from the short variant protein could be detected around 15 kDa in either hetero-deficient or homo-deficient mice (FIG. 6). Therefore, it was confirmed that at least no active LLPL protein was produced in homo-deficient mice. Although an incomplete mRNA is synthesized in the deficient mice created this time, it is believed that the protein produced from such mRNA is unstable and does not exist.

Figure 8:
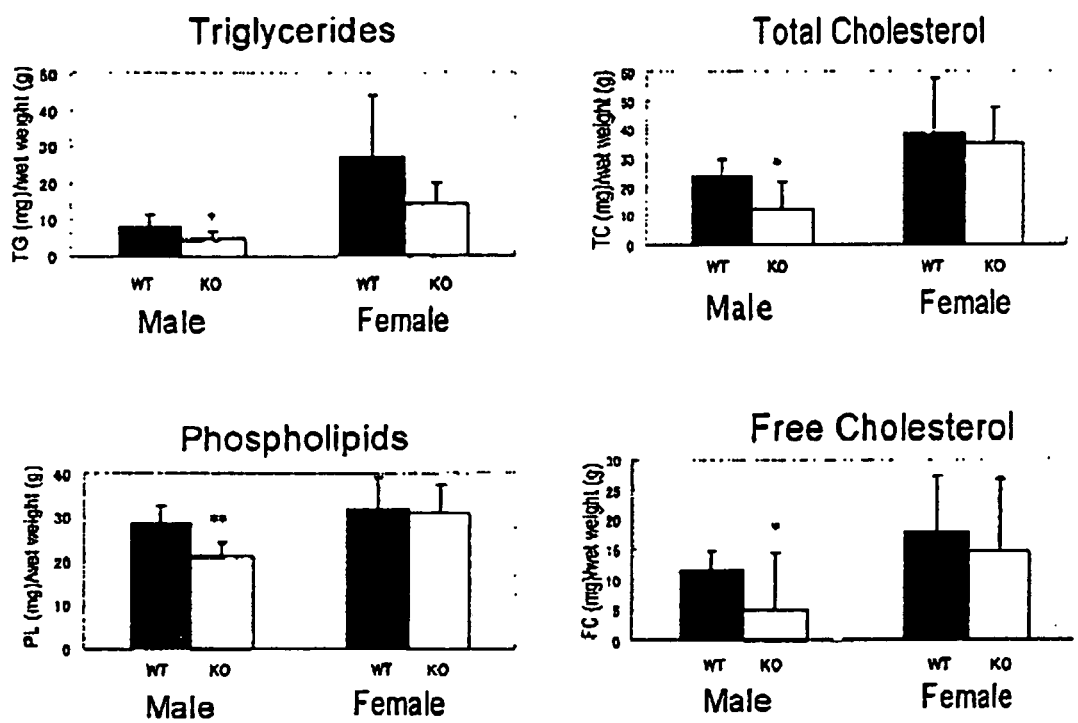
FIG. 8 shows lipid contents per wet weight in each group.

No particular abnormalities were recognized in the appearance of the LLPL homo-deficient mice, and no definite difference was recognized in the body weight among the homo-deficient, hetero-deficient and wild-type groups. The third generation male and female LLPL homo-deficient mice derived from LLPL gene deficient ES cell clone LX-2-163 and wild-type mice were fed with a normal diet or a high fat high cholesterol diet for 16 weeks starting from the age of 6 weeks. As a result, plasma cholesterol levels in the LLPL homo-deficient mice fed with a normal diet tended to be lower than the wild-type mice fed with the same diet, though there was no significant difference. On the other hand, when a high fat high cholesterol diet was given, total cholesterol levels and LDL+VLDL cholesterol levels in the plasma as well as triglyceride levels, phospholipid levels, free cholesterol levels and total cholesterol levels in the liver and liver weights were increased in both the LLPL homo-deficient mice and wild-type mice. However, in any of the above items, the LLPL homo-deficient mice tended to show lower values than the wild-type mice. This phenomenon was more definite in male mice than female mice. Histopathological examinations revealed the following findings of fatty liver in hepatocytes of the LLPL homo-deficient mice and wild-type mice: increase in vacuoles and disturbance of the trabecular structure due to excessive fat accumulation, increase in single cell necrosis, varied sizes of nuclei and mononuclear cell infiltration caused by the feeding of high fat high cholesterol diet for 16 weeks. The degrees of these fatty liver findings were also lighter in LLPL homo-deficient male mice than wild-type male mice (FIG. 7), which was consistent with the findings of blood lipid and liver lipid. With respect to the lipid contents of the liver in homo-deficient male mice, the contents of triglycerides, phospholipids and free cholesterol were significantly lower than the contents in the wild-type mice (FIG. 8).

Example 5

Creation of LLPL/ApoE Double-Deficient Mice

LLPL deficient male homozygous mice (LLPL$^{-/-}$) were mated with ApoE deficient female homozygous mice (ApoE$^{-/-}$) to create F1 heterozygous deficient mice (LLPL$^{+/-}$/ApoE$^{+/-}$). Subsequently, these F1 hetero-deficient mice were mated among them to obtain F2 mice. From these F2 mice, wild-type mice (LLPL$^{+/+}$/ApoE$^{+/+}$), LLPL deficient mice (LLPL$^{-/-}$/ApoE$^{+/+}$), ApoE deficient mice (LLPL$^{+/+}$/ApoE$^{-/-}$) and LLPL/ApoE double-deficient mice (LLPL$^{-/-}$/ApoE$^{-/-}$) were selected by PCR judgment. Thereafter, mice were produced by mating the above-described individuals within the same group.

Example 6

Figure 10:
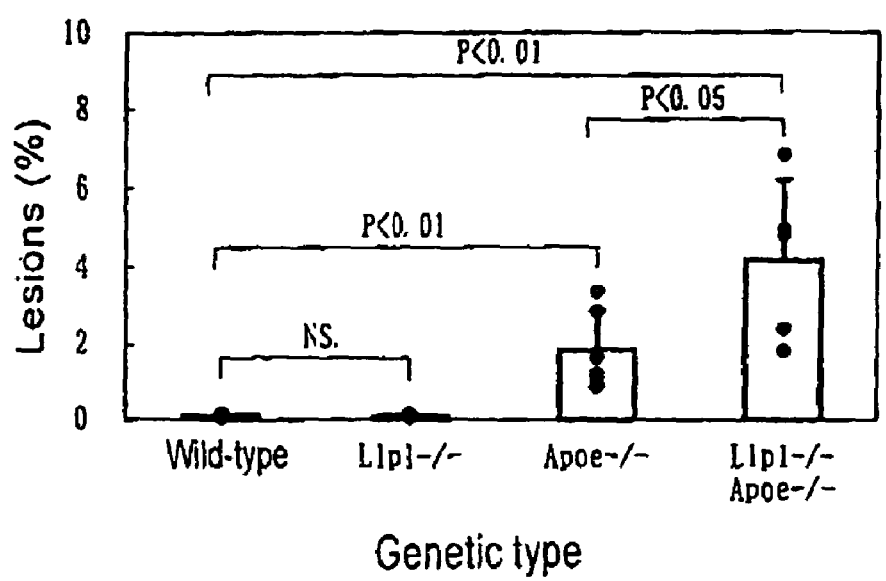
FIG. 10 shows comparison of the ratios of arteriosclerotic lesion areas lipid-stained with Sudan IV in the aorta of LLPL/ApoE double-deficient mice, ApoE deficient mice, LLPL deficient mice and wild-type mice (18-week old male).
Figure 11:
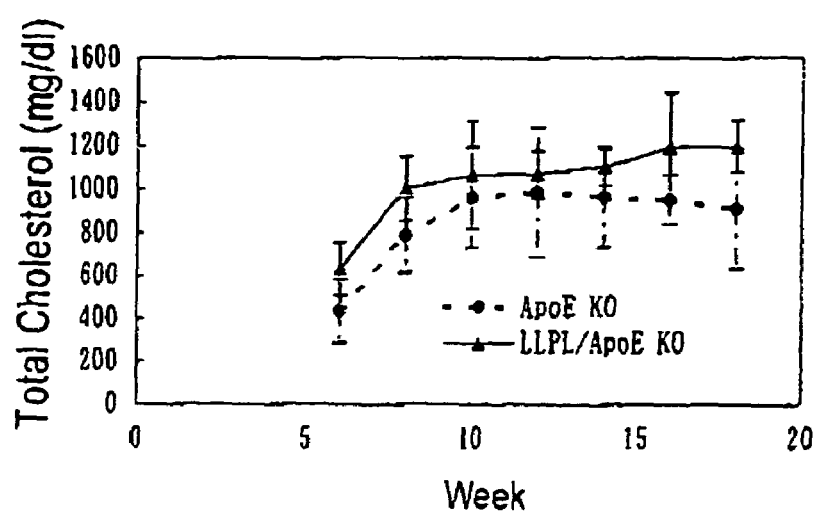
FIG. 11 shows the time course of total plasma cholesterol levels in LLPL/ApoE double-deficient mice and ApoE deficient mice (18-week old male).

Evaluation of Arteriosclerotic Lesions in the Aorta of LLPL/ApoE Double-Deficient Male Mice Four male mouse groups of wild-type mice (LLPL$^{+/+}$/ApoE$^{+/+}$), LLPL deficient mice (LLPL$^{-/-}$/ApoE$^{+/+}$), ApoE deficient mice (LLPL$^{+/+}$/ApoE$^{-/-}$) and LLPL/ApoE double-deficient mice (LLPL$^{-/-}$/ApoE$^{-/-}$) were fed with a normal diet (CE-2 solid feed: CLEA Japan Inc.) The mice were slaughtered by cutting the head at the age of 18 weeks, and the heart and the aorta were collected from each mouse. Briefly, after the slaughter, internal organ tissues such as liver, small intestine, lung, lipids, etc. were removed roughly. Paraaortic lipids and connective tissues from the arch to the thigh were removed by a stereomicroscope. Then, the aorta was cut open from the belly towards the arch of the aorta and the thigh, and taken out by cutting off its root in the heart and the branched portion of the thigh. The thus obtained aorta, was placed in physiological saline. The lipid tissues and connective tissues adhering to the outside of the aorta, as well as coagulated blood were removed carefully. Then, the aorta was fixed on a black rubber plate with setting pins with its lumen upside, to thereby prepare a specimen. Arteriosclerotic lesions in the thus prepared specimen were lipid-stained with Sudan IV. Briefly, the specimen together with the rubber plate was rinsed lightly with 70% ethanol, then soaked in 0.5% Sudan IV solution (acetone:EtOH:H$_2$O=1:1:1) and stained for 30 min. After de-staining with 70% ethanol and washing with water, the specimen was fixed in 4% formalin//PBS, and photographs of the lipid-stained specimen were taken with a digital camera. The thus obtained images were analyzed with MacScope (an application for image analysis) to thereby quantitatively determine the total area of the specimen and the area of lesions. FIG. 10 shows the ratio of the area of lesions in the aorta specimen in each group.

In wild-type mice (LLPL$^{+/+}$/ApoE$^{+/+}$) and LLPL deficient mice (LLPL$^{-/-}$/ApoE$^{+/+}$), formation of arteriosclerotic lesions was not observed at all. While the ratio of the area of arteriosclerotic lesions in ApoE deficient mice (LLPL$^{+/+}$/ApoE$^{-/-}$: n=6) was (1.8±1.0)%, the ratio in LLPL/ApoE double-deficient mice (LLPL$^{-/-}$/ApoE$^{-/-}$: n=5) was (4.2±2.10)%. A significant increase of 2.3-fold was observed ($P<0.05$; by Dunnett test).

Example 7

Transition of Plasma Total Cholesterol Levels in LLPL/ApoE Double-Deficient Male Mice Blood samples were collected from the orbital venous plexus of the mice used in the experiments in Example 6 at the ages of 6, 8, 10, 12, 14, 16 and 18 weeks using a heparin sodium-added glass capillary. FIG. 1 shows the data for ApoE deficient mice (LLPL$^{+/+}$/ApoE$^{-/-}$) and LLPL/ApoE double-deficient mice (LLPL$^{-/-}$/ApoE$^{-/-}$). The changes in plasma cholesterol levels from age 6 to 18 weeks in both groups exhibited a tendency that the plasma total cholesterol levels in LLPL/ApoE double-deficient mice were slightly higher.

Example 8

Figure 12:
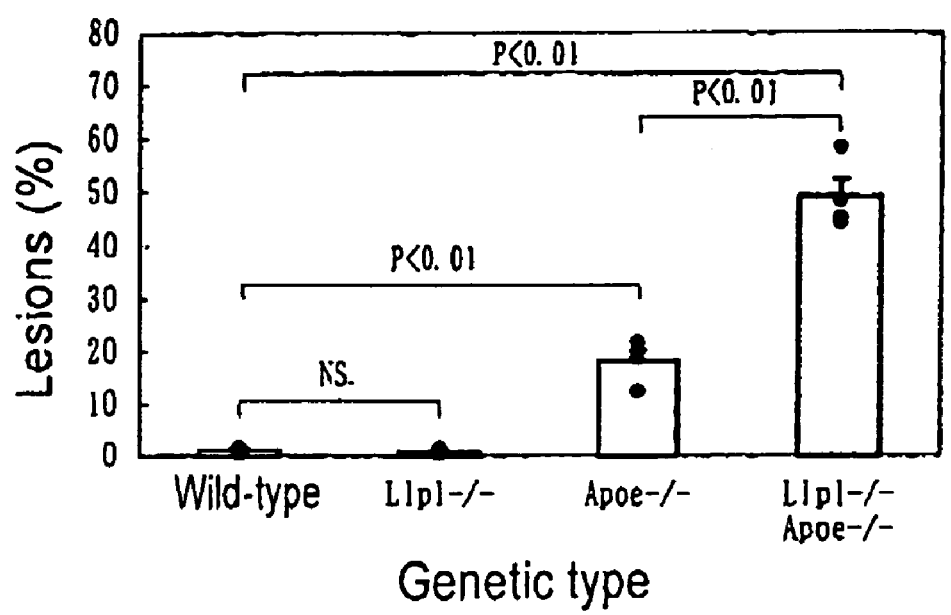
FIG. 12 shows comparison of the ratios of arteriosclerotic lesion areas lipid-stained with Sudan IV in the aorta of LLPL/ApoE double-deficient mice, ApoE deficient mice, LLPL deficient mice and wild-type mice (38-week old female).
Figure 13:
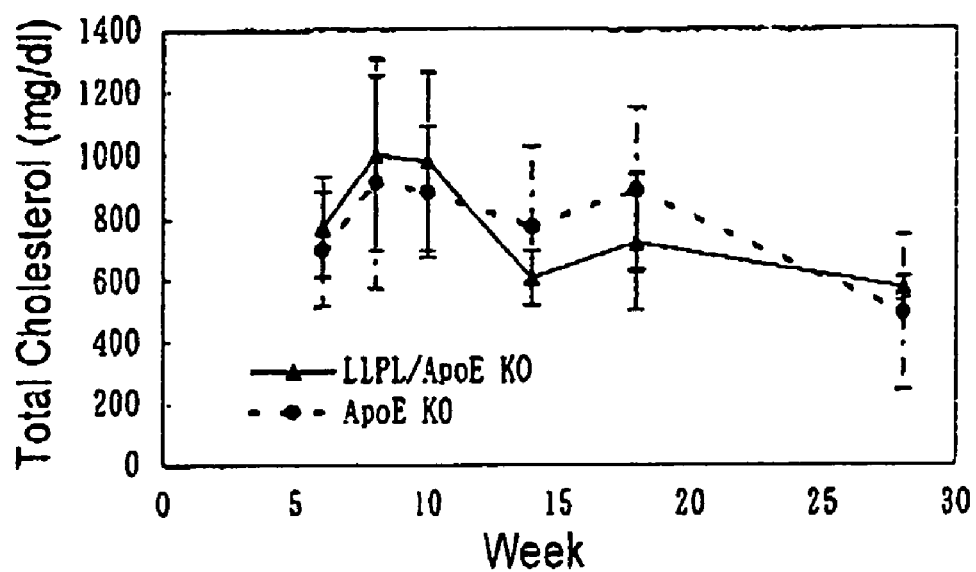
FIG. 13 shows the time course of total plasma cholesterol levels in LLPL/ApoE double-deficient mice and ApoE deficient mice (38-week old female).

Evaluation of Arteriosclerotic Lesions in the Aorta of LLPL/ApoE Double-Deficient Female Mice Four female mouse groups of wild-type mice (LLPL$^{+/+}$/ApoE$^{+/+}$), LLPL deficient mice (LLPL$^{-/-}$/ApoE$^{+/+}$), ApoE deficient mice (LLPL$^{+/+}$/ApoE$^{-/-}$) and LLPL/ApoE double-deficient mice (LLPL$^{-/-}$/ApoE$^{-/-}$) were fed with a normal diet (CE-2 solid feed: CLEA Japan Inc.) up to the age of 38 weeks. The mice were slaughtered by cervical dislocation at that age, and the aorta was collected from each mouse. The colleting of the aorta and lipid staining were performed based on the methods as described in Example 5. FIG. 12 shows the ratio of the area of lesions in the aorta specimen in each group.

In wild-type mice (LLPL$^{+/+}$/ApoE$^{+/+}$) and LLPL deficient mice (LLPL$^{-/-}$/ApoE$^{+/+}$), formation of arteriosclerotic lesions was not observed as in the corresponding male mice at the age of 18 weeks. While the ratio of the area of arteriosclerotic lesions in ApoE deficient mice (LLPL$^{+/+}$/ApoE$^{-/-}$: n=4) was (18.3±2.1)%, the ratio in LLPL/ApoE double-deficient mice (LLPL$^{-/-}$/ApoE$^{-/-}$: n=4) was (49.3±3.2)%. A significant increase of 2.7-fold was observed (P<0.01; by Dunnett test).

Example 9

Transition of Plasma Total Cholesterol Levels in LLPL/ApoE Double-Deficient Female Mice Blood samples were also collected from the orbital venous plexus of the mice used in the experiments in Example 8 at the ages of 6, 8, 10, 14, 18 and 28 weeks using a heparin sodium-added glass capillary. Plasma cholesterol levels up to the age of 28 weeks in the two groups of wild-type mice (LLPL$^{+/+}$/ApoE$^{+/+}$) and LLPL deficient mice (LLPL$^{-/-}$/ApoE$^{+/+}$) showed almost similar transition; and those levels in the two groups of ApoE deficient mice (LLPL$^{+/+}$/ApoE$^{-/-}$) and LLPL/ApoE double-deficient mice (LLPL$^{-/-}$/ApoE$^{-/-}$) also showed almost similar transition. No significant difference was observed between either of the two groups. The data for ApoE deficient mice (LLPL$^{+/+}$/ApoE$^{-/-}$) and LLPL/ApoE double-deficient mice (LLPL$^{-/-}$/ApoE$^{-/-}$) are shown in FIG. 4.

INDUSTRIAL APPLICABILITY

The non-human animal ES cell of the invention in which its LLPL gene is inactivated is very useful in creating a non-human animal deficient in expression of LLPL gene.

The LLPL expression deficient non-human animal of the invention can be a disease model for such diseases caused by inactivation of the biological activities induced by LLPL since the animal lacks various biological activities inducible by LLPL. Therefore, the animal of the invention is useful in screening for prophylactic and/or therapeutic drug for various diseases resulting from LLPL deficiency, as well as in elucidating the causes of LLPL-related diseases and examining therapeutic methods for such diseases.

Further, the double function deficient model animal created by mating the LLPL expression deficient non-human animal of the invention with an arteriosclerosis model animal is useful in examining relationships with diseases caused by the arteriosclerosis-related gene ApoE, screening for prophylactic and/or therapeutic drug for various diseases resulting from LLPL deficiency or ApoE deficiency, as well as in elucidating the causes of LLPL and ApoE-related diseases and examining therapeutic methods for such diseases.

With the LLPL gene-transferred non-human animal of the invention, it is possible to elucidate the disease mechanisms of LLPL-related diseases, such as hyper-LLPL disease and LLPL insufficiency, and to examine therapeutic methods for such diseases. Further, the above animal of the invention may be used in screening for therapeutic drug for the above-described LLPL-related diseases. According to the screening method of the invention, it is possible to efficiently screen for prophylactic and/or therapeutic drug for various diseases resulting from LLPL deficiency.

The invention claimed is:

1. A knockout transgenic mouse whose genome comprises a deletion in the endogenous lecithin:cholesterol acyltransferase-like lysophospholipase gene encoding the amino acid sequence of SEQ ID NO: 1, wherein plasma cholesterol levels in the said mouse is lower than wild-type mouse.

2. A method of screening for a prophylactic and/or therapeutic drug for arteriosclerosis, comprising administering a test compound to the mouse, according to claim 1 and evaluating the effect of the test compound on arteriosclerosis.

3. An arteriosclerosis model mouse, an isolated tissue thereof or isolated cells thereof, wherein the mouse is double-deficient in lecithin:cholesterol acyltransferase-like lysophospholipase gene encoding the amino acid sequence of SEQ ID NO: 1 and apolipoprotein gene.

4. A method of screening for a prophylactic and/or therapeutic drug for arteriosclerosis, comprising administering a test compound to the mouse, an isolated tissue thereof or isolated cells derived from the mouse according to claim 3 and evaluating the effect of the test compound on arteriosclerosis.

* * * * *